US012697053B2

(12) United States Patent
Chen et al.

(10) Patent No.: US 12,697,053 B2
(45) Date of Patent: Aug. 4, 2026

(54) METHODS AND SYSTEMS FOR PROVIDING CALIBRATION POINT ACCEPTANCE CRITERIA FOR CALIBRATING AN ANALYTE SENSOR

(71) Applicant: Senseonics, Incorporated, Germantown, MD (US)

(72) Inventors: Xiaoxiao Chen, Washington, DC (US); Andrew Dehennis, Germantown, MD (US); Srinivasan Rajaraman, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 375 days.

(21) Appl. No.: 18/449,623

(22) Filed: Aug. 14, 2023

(65) Prior Publication Data

US 2024/0041368 A1     Feb. 8, 2024

Related U.S. Application Data

(62) Division of application No. 16/009,922, filed on Jun. 15, 2018, now Pat. No. 11,723,565.

(Continued)

(51) Int. Cl.
*A61B 5/1495*        (2006.01)
*A61B 5/00*        (2006.01)
(Continued)

(52) U.S. Cl.
CPC .......... *A61B 5/1495* (2013.01); *A61B 5/0031* (2013.01); *A61B 5/14503* (2013.01);
(Continued)

(58) Field of Classification Search
CPC .......... A61B 2560/0223; A61B 5/1495; A61B 5/14503; A61B 5/14532; A61B 5/1459
(Continued)

(56) References Cited

U.S. PATENT DOCUMENTS 6,895,263 B2    5/2005    Shin et al.
7,783,442 B2    8/2010    Mueller, Jr. et al.
(Continued)

FOREIGN PATENT DOCUMENTS

EP        2335584 A1    6/2011
EP        2329770 B1    9/2014
(Continued)

*Primary Examiner* — Puya Agahi
(74) *Attorney, Agent, or Firm* — Rothwell, Figg, Ernst & Manbeck, P.C.

(57)        ABSTRACT

A method and transceiver for calibrating an analyte sensor using one or more reference measurements. In some embodiments, the method may include receiving a first reference analyte measurement (RM1) and determining whether the RM1 is unexpected. In some embodiments, the method may include, if the RM1 was determined to be unexpected, receiving a second reference analyte measurement (RM2). In some embodiments, the method may include determining whether one or more of the RM1 and the RM2 are acceptable as calibration points. In some embodiments, the method may include, if one or more of the RM1 and the RM2 are determined to be acceptable as calibration points, accepting one or more of the RM1 and the RM2 as calibration points. In some embodiments, the method may include calibrating the analyte sensor using at least one or more of the RM1 and the RM2 as calibration points.

21 Claims, 14 Drawing Sheets

50

Sensor (subcutaneous) 100     Body-Worn Transmitter 101     Smartphone with Mobile Medical App 105

Related U.S. Application Data

(60) Provisional application No. 62/520,852, filed on Jun. 16, 2017.

(51) Int. Cl.

| | |
|---|---|
| *A61B 5/145* | (2006.01) |
| *A61B 5/1459* | (2006.01) |
| *A61B 5/15* | (2006.01) |
| *A61B 5/151* | (2006.01) |
| *G01N 33/66* | (2006.01) |
| *G01N 33/96* | (2006.01) |

(52) U.S. Cl.
CPC ........ *A61B 5/14532* (2013.01); *A61B 5/1459* (2013.01); *A61B 5/150022* (2013.01); *A61B 5/686* (2013.01); *A61B 5/742* (2013.01); *G01N 33/66* (2013.01); *G01N 33/96* (2013.01); *A61B 5/0004* (2013.01); *A61B 5/0026* (2013.01); *A61B 5/15142* (2013.01); *A61B 2560/0223* (2013.01); *A61B 2560/0252* (2013.01)

(58) Field of Classification Search
USPC .................... 600/365; 702/85, 104; 73/1.01
See application file for complete search history.

(56) References Cited

U.S. PATENT DOCUMENTS

| | | | |
|---|---|---|---|
| 7,890,295 | B2 | 2/2011 | Shin et al. |
| 8,073,548 | B2 | 12/2011 | Colvin, Jr. et al. |
| 8,160,669 | B2 | 4/2012 | Brauker et al. |
| 8,515,516 | B2 | 8/2013 | Kamath et al. |
| 8,684,930 | B2 | 4/2014 | Feldman et al. |
| 9,414,775 | B2 | 8/2016 | Colvin, Jr. et al. |
| 9,693,714 | B2 | 7/2017 | DeHennis et al. |
| 2006/0019327 | A1 | 1/2006 | Brister et al. |
| 2007/0016381 | A1 | 1/2007 | Kamath et al. |
| 2011/0184268 | A1 | 7/2011 | Taub |
| 2013/0241745 | A1 | 9/2013 | Colvin, Jr. et al. |
| 2014/0182350 | A1 | 7/2014 | Bhavaraju et al. |
| 2014/0242622 | A1* | 8/2014 | Petrich ................. A61B 5/1495 435/26 |
| 2017/0071511 | A1 | 3/2017 | Garcia et al. |

FOREIGN PATENT DOCUMENTS

| | | |
|---|---|---|
| WO | 03/094714 A1 | 11/2003 |
| WO | 2016/191715 A1 | 12/2016 |

* cited by examiner

50

METHODS AND SYSTEMS FOR PROVIDING CALIBRATION POINT ACCEPTANCE CRITERIA FOR CALIBRATING AN ANALYTE SENSOR

CROSS-REFERENCE TO RELATED APPLICATION

The present application is a divisional of U.S. application Ser. No. 16/009,922, filed Jun. 15, 2018, which claims the benefit of priority to U.S. Provisional Application Ser. No. 62/520,852, filed on Jun. 16, 2017, which are each incorporated herein by reference in their entireties.

BACKGROUND

Field of Invention

The present invention relates to calibrating an analyte sensor in an analyte monitoring system. More specifically, aspects of the present invention relate to determining whether a reference measurement is acceptable for calibrating the analyte sensor.

Discussion of the Background

Analyte monitoring systems may be used to measure analyte levels, such as analyte concentrations. One type of analyte monitoring system is a continuous glucose monitoring (CGM) system. A CGM system measures glucose levels throughout the day and can be very useful in the management of diabetes. Analyte monitoring systems require calibration (and re-calibration) to maintain sensor accuracy and sensitivity. The calibration may be, for example and without limitation, performed daily or twice-daily. The calibration may be performed using reference measurements. The reference measurements may be, for example and without limitation, self-monitoring blood glucose (SHBG) measurements. The reference measurements may be, for example and without limitation, obtained from finger-stick blood samples.

At least in the home environment, reference measurements are frequently erroneous. If an analyte monitoring system performs calibration using an erroneous analyte measurement as a calibration point, the analyte monitoring system may produce analyte measurements that are erroneous and inaccurate. Accordingly, systems and methods that prevent inaccurate reference measurements from negatively affecting calibration are needed.

One method for determining whether to accept or reject a reference measurement as a calibration point considers one or more of (i) whether the reference measurement is within the display range of the analyte monitoring system and (ii) whether the rate of change of the most recent analyte measurement taken by the analyte monitoring system is slow enough for calibration. When the reference measurement is a glucose measurement, the display range of the analyte monitoring system may be, for example and without limitation, between 40 and 400 mg/dL. When the reference measurement is a glucose measurement, the rate of change range acceptable for calibration may be, for example and without limitation, between −2.5 mg/dL/min and 2.5 mg/dL/min. If one or more of the reference measurement and the rate of change criteria is not satisfied, then the analyte monitoring system may reject the reference measurement. This may eliminate the most inaccurate of the erroneous reference measurements from being used as calibration points. However, inaccurate reference measurements within the display range of the analyte monitoring system are not prevented from negatively affecting the calibration process. Accordingly, improved methods and analyte monitoring systems are needed to improve calibration reliability and the accuracy of analyte measurements.

SUMMARY

Aspects of the present invention relate to improving calibration reliability and analyte measurement accuracy by identifying erroneous reference measurements and excluding them from use as calibration points. Even a reference measurement within the display range of the analyte monitoring system may have a large error. If calibration were performed using an inaccurate reference measurement, the error in the reference measurement would cause errors in the calculation of subsequent analyte measurements using sensor data received from an analyte sensor. Aspects of the present invention may relate to a calibration point acceptance process that may prevent erroneous reference measurements from being used as calibration points and, thereby, improve accuracy of sensor measurements. The improvement in sensor measurement accuracy may limit the number of false alerts related to high or low analyte levels, which may be especially helpful overnight when a user is trying to sleep.

One aspect of the invention may provide a method of calibrating an analyte sensor using one or more reference measurements. The method may include receiving a first reference analyte measurement (RM1). The method may include determining that the RM1 is unexpected. The method may include, after determining that the RM1 is unexpected, receiving a second reference analyte measurement (RM2). The method may include determining that one or more of the RM1 and the RM2 are acceptable as calibration points. The method may include accepting one or more of the RM1 and the RM2 as calibration points. The method may include calibrating the analyte sensor using at least one or more of the RM1 and the RM2 as calibration points.

In some embodiments, the RM1 may be a self-monitoring blood glucose (SMBG) measurement obtained from a finger-stick blood sample. In some embodiments, determining that the RM1 is unexpected may include determining that the RM1 is not within a threshold amount of a sensor analyte measurement.

In some embodiments, the method may include one or more of receiving sensor data from the analyte sensor, using the sensor data to calculate a first sensor analyte measurement (SM1) without RM1 as a calibration point, and using the sensor data to calculate a second sensor analyte measurement (SM2) with the RM1 as a calibration point. In some embodiments, determining that one or more of the RM1 and the RM2 are acceptable as calibration points may include comparing the RM2 with one or more of the SM1 and the SM2. In some embodiments, determining that one or more of the RM1 and the RM2 are acceptable as calibration points may include determining that the difference between the RM2 and the SM2 is within a threshold amount, and determining that the RM2 is closer to the SM2 than to the SM1. In some embodiments, accepting one or more of the RM1 and the RM2 as calibration points may include accepting both the RM1 and the RM2 as calibration points. In some embodiments, calibrating the analyte sensor may use at least the RM1 and the RM2 as calibration points.

In some embodiments, determining that one or more of the RM1 and the RM2 are acceptable as calibration points may include one or more of determining that the difference between the RM2 and the SM1 is within the threshold amount; and determining that the RM2 is closer to the SM1 than to the SM2. In some embodiments, accepting one or more of the RM1 and the RM2 as calibration points may include accepting the RM2 as a calibration point and not accepting the RM1 as a calibration point. In some embodiments, calibrating the analyte sensor may use at least the RM2 as a calibration point and may not use the RM1 as a calibration point.

In some embodiments, accepting one or more of the RM1 and the RM2 as calibration points may include storing one or more of the RM1 and the RM2 in a calibration point memory. In some embodiments, calibrating the analyte sensor may include calibrating a conversion function used to convert sensor data received from the analyte sensor into a sensor analyte measurement. In some embodiments, the method may include storing the unexpected RM1 in a calibration point memory. In some embodiments, determining that one or more of the RM1 and the RM2 are acceptable as calibration points may include determining that the RM2 is acceptable and that the RM1 is not acceptable. In some embodiments, the method may include, in response to determining that RM1 is not acceptable, deleting the RM1 from the calibration point memory.

Another aspect of the invention may provide a method of calibrating an analyte sensor using one or more reference measurements. The method may include receiving a first reference analyte measurement (RM1). The method may include determining that the RM1 is unexpected. The method may include, after determining that the RM1 is unexpected, receiving a second reference analyte measurement (RM2). The method may include determining that the RM2 is unexpected. The method may include, after determining that the RM2 is unexpected, receiving a third reference analyte measurement (RM3). The method may include accepting one or more of the RM2 and the RM3 as calibration points. The method may include calibrating the analyte sensor using at least one or more of the RM2 and the RM3 as calibration points.

In some embodiments, the method may include, after determining that the RM2 is unexpected, accepting the RM1. In some other embodiments, the method may include, after determining that the RM2 is unexpected, rejecting the RM1.

Yet another aspect of the invention may provide a transceiver including a sensor interface device, a display interface device, and a processor. The sensor interface device may be configured to receive sensor data conveyed by an analyte sensor. The display interface device may be configured to convey information to a display device and to receive information from the display device. The processor may be configured to receive a first reference analyte measurement (RM1) from the display device via the display interface device. The processor may be configured to determine that the RM1 is unexpected. The processor may be configured to, after determining that the RM1 is unexpected, receive a second reference analyte measurement (RM2) from the display device via the display interface device. The processor may be configured to determine that one or more of the RM1 and the RM2 are acceptable as calibration points. The processor may be configured to accept one or more of the RM1 and the RM2 as calibration points. The processor may be configured to calibrate the analyte sensor using at least one or more of the RM1 and the RM2 as calibration points.

Still another aspect of the invention may provide a transceiver including a sensor interface device, a display interface device, and a processor. The sensor interface device may be configured to receive sensor data conveyed by the analyte sensor. The display interface device may be configured to convey information to a display device and to receive information from the display device. The processor may be configured to receive a first reference analyte measurement (RM1) from the display device via the display interface device. The processor may be configured to determine that the RM1 is unexpected. The processor may be configured to, after determining that the RM1 is unexpected, receive a second reference analyte measurement (RM2) from the display device via the display interface device. The processor may be configured to determine that the RM2 is unexpected. The processor may be configured to, after determining that the RM2 is unexpected, receive a third reference analyte measurement (RM3) from the display device via the display interface device. The processor may be configured to accept one or more of the RM2 and the RM3 as calibration points. The processor may be configured to calibrate the analyte sensor using at least one or more of the RM2 and the RM3 as calibration points.

In some embodiments, the processor may be further configured to, after determining that the RM2 is unexpected, accept the RM1. In other embodiments, the processor may be further configured to, after determining that the RM2 is unexpected, reject the RM1.

Another aspect of the invention may provide a method including receiving one or more reference analyte measurements at a first rate. The method may include determining that a first reference analyte measurement (RM1) of the one or more reference analyte measurements received at the first rate is an expected reference analyte measurement. The method may include, after determining that the RM1 is an expected reference analyte measurement, receiving one or more reference analyte measurements at a second rate, wherein second rate is lower than the first rate.

In some embodiments, the method may further include determining that a second reference analyte measurement (RM2) of the one or more reference analyte measurements received at the second rate is not an expected reference analyte measurement and, after determining that the RM2 is not an expected reference analyte measurement, receiving one or more reference analyte measurements at the first rate. In some embodiments, determining that the RM1 is an expected reference analyte measurement may include determining that the RM1 is within a threshold amount of a sensor analyte measurement.

In some embodiments, the method may further include, before determining that the RM1 is an expected reference analyte measurement, causing a display device to prompt a user for reference measurements at the first rate. In some embodiments, the method may further include, after determining that the RM1 is an expected reference analyte measurement, causing a display device to prompt a user for reference measurements at the second rate. In some embodiments, the method may further include performing a calibration using the RM1 as a calibration point.

Still another aspect of the invention may provide a transceiver including a display interface device and a processor. The display interface device may be configured to convey information to a display device and to receive information from the display device. The processor may be configured to receive one or more reference analyte measurements from the display device via the display interface device at a first rate. The processor may be configured to determine whether a first reference analyte measurement (RM1) of the one or more reference analyte measurements received at the first rate is an expected reference analyte measurement. The processor may be configured to, after determining that the RM1 is an expected reference analyte measurement, receive one or more reference analyte measurements from the display device via the display interface device at a second rate, wherein second rate is lower than the first rate.

In some embodiments, the processor may be further configured to determine that a second reference analyte measurement (RM2) of the one or more reference analyte measurements received at the second rate is not an expected reference analyte measurement and, after determining that the RM2 is not an expected reference analyte measurement, receive one or more reference analyte measurements from the display device via the display interface device at the first rate. In some embodiments, the transceiver may further include a sensor interface device configured to receive sensor data conveyed by an analyte sensor, and determining that the RM1 is an expected reference analyte measurement may include determining that the RM1 is within a threshold amount of a sensor analyte measurement calculated using the sensor data received from the analyte sensor via the sensor interface device.

In some embodiments, the processor may be further configured to, before determining that the RM1 is an expected reference analyte measurement, cause a display device to prompt a user for reference measurements at the first rate. In some embodiments, the processor may be further configured to, after determining that the RM1 is an expected reference analyte measurement, cause a display device to prompt a user for reference measurements at the second rate. In some embodiments, the processor may be further configured to perform a calibration using the RM1 as a calibration point.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

6

Figure 9:
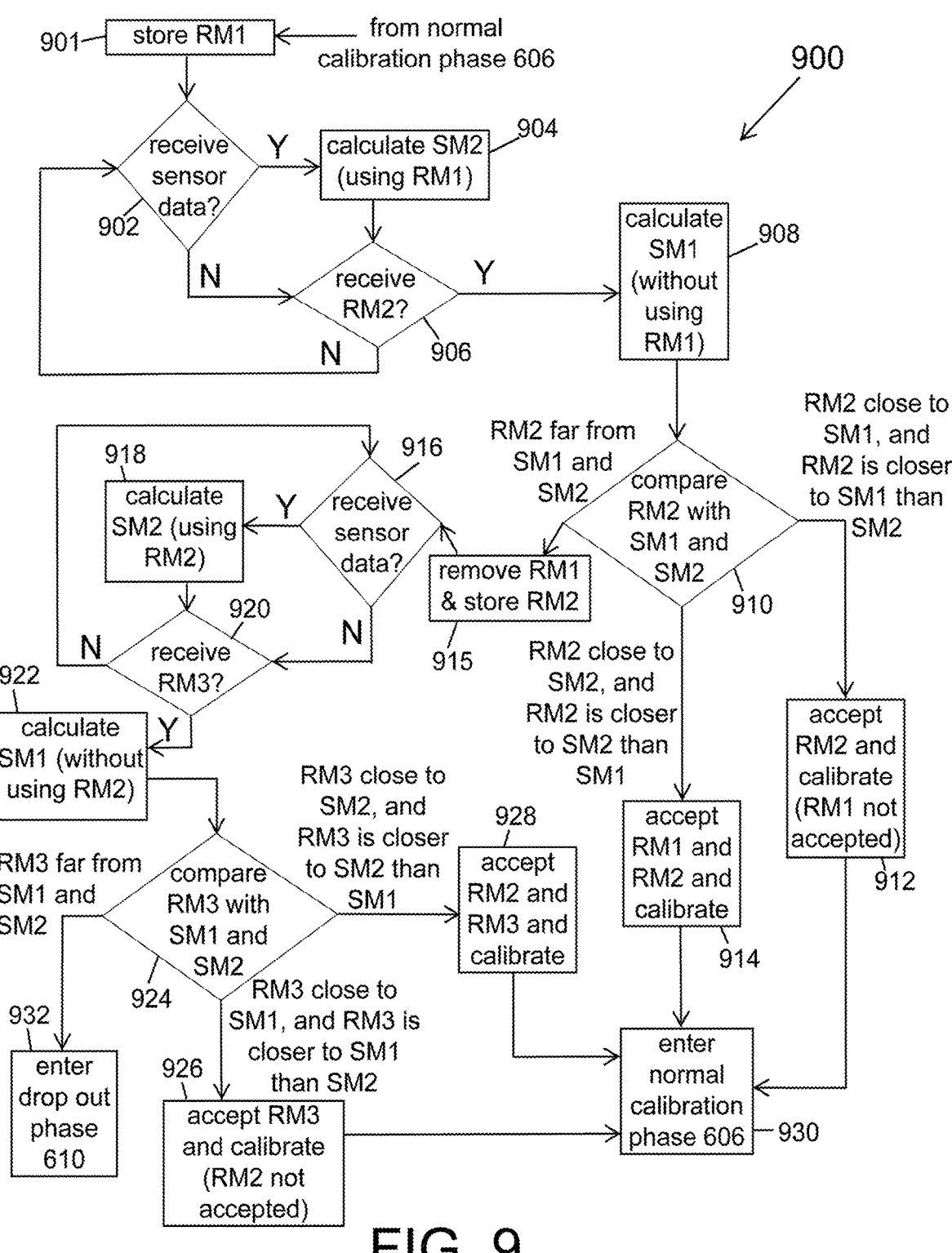

FIG. 9 is a flow chart illustrating an alternative unexpected calibration process embodying aspects of the present invention.

Figure 10:
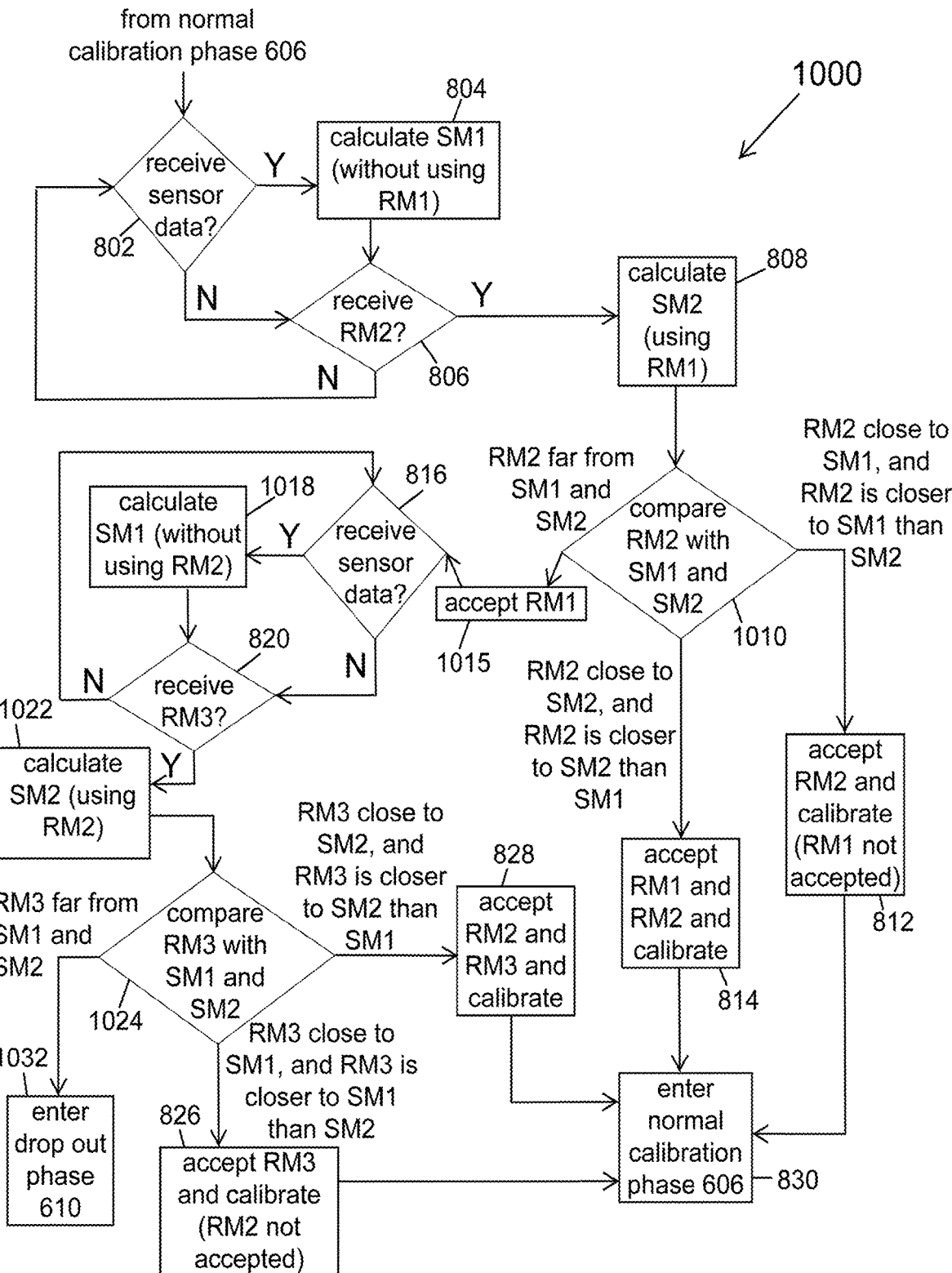

FIG. 10 is a flow chart illustrating another alternative unexpected calibration process embodying aspects of the present invention.

Figure 11:
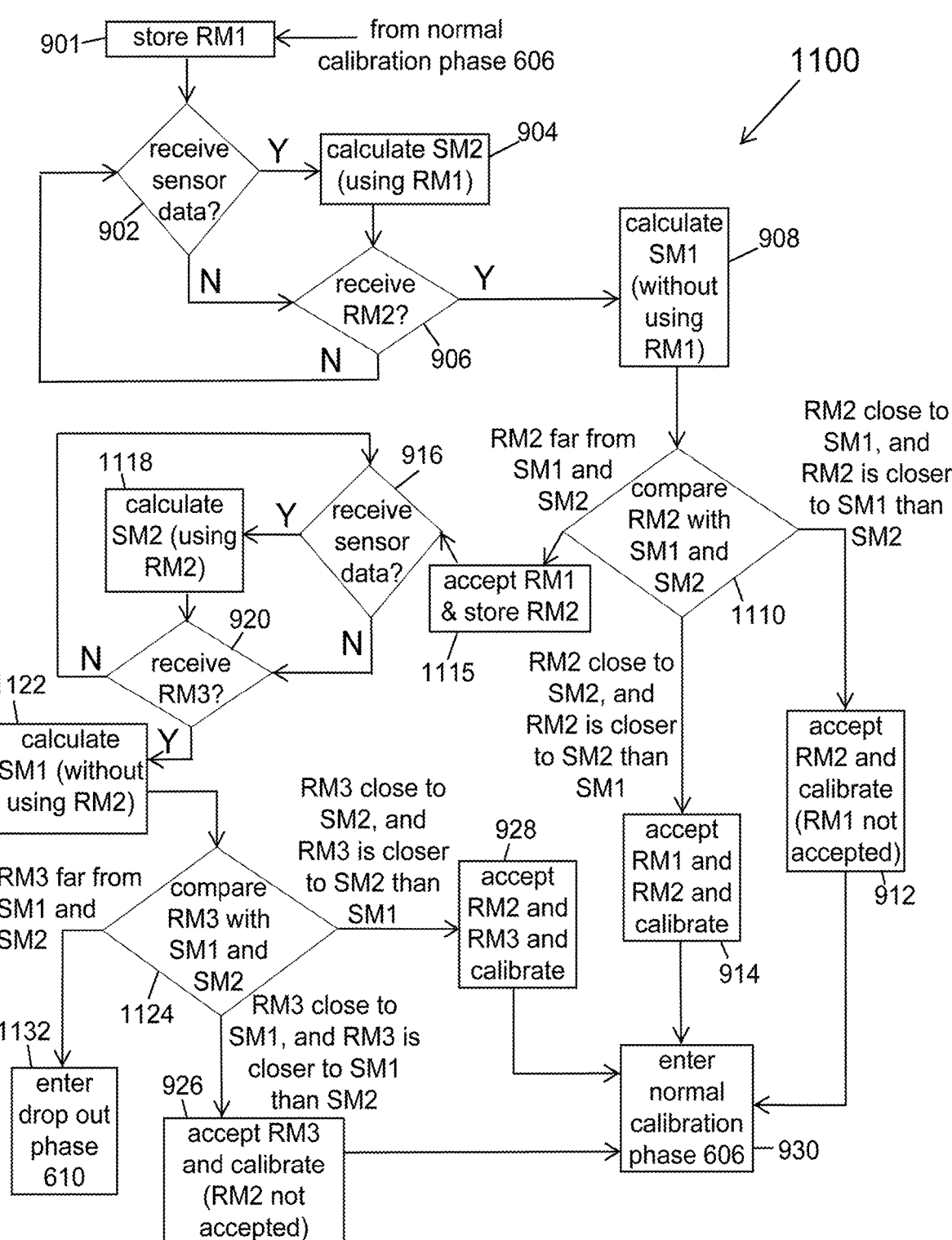

FIG. 11 is a flow chart illustrating an additional alternative unexpected calibration process embodying aspects of the present invention.

Figure 12:
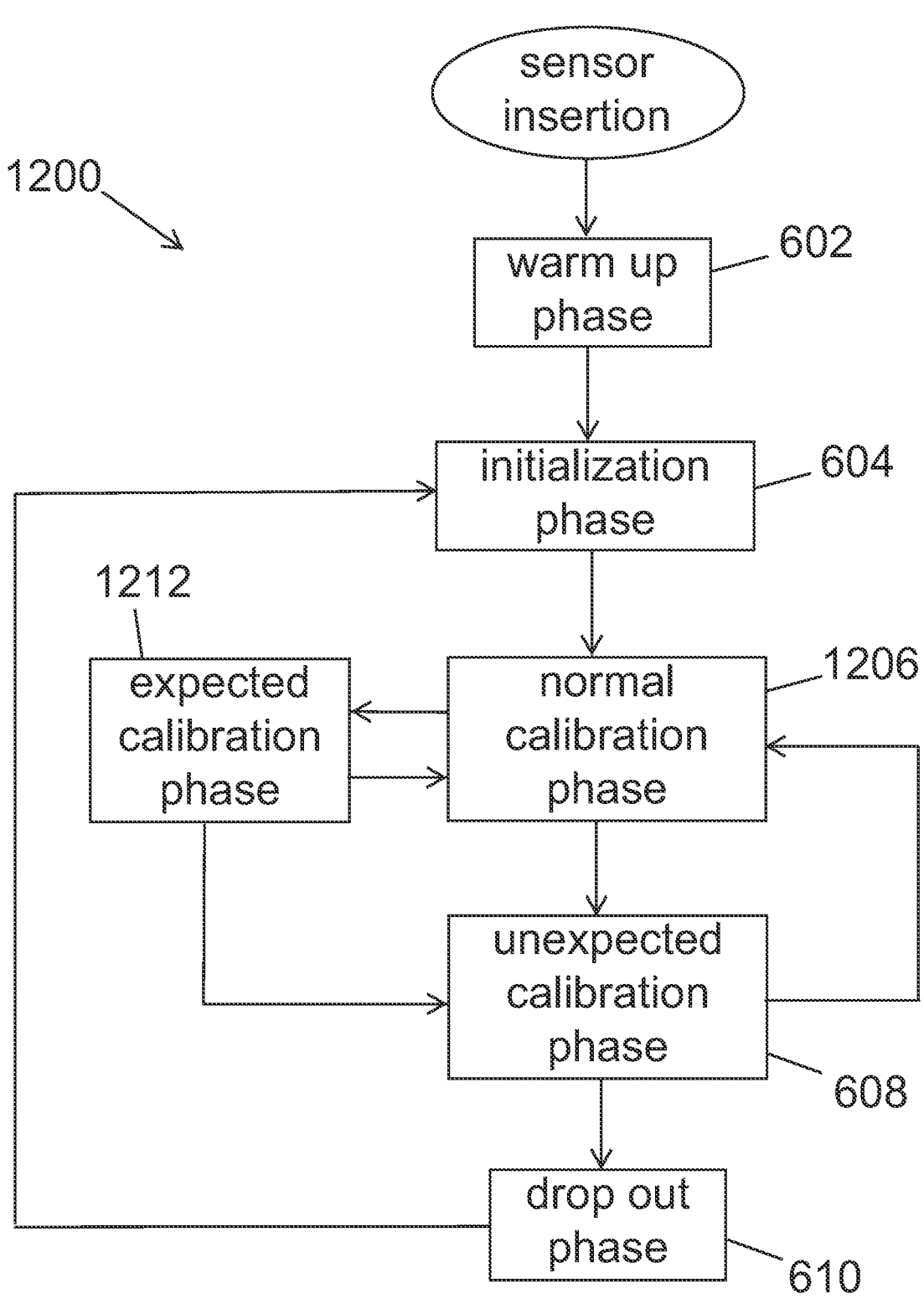

FIG. 12 is a flow chart illustrating an alternative process for controlling initialization and calibration of an analyte monitoring system embodying aspects of the present invention.

Figure 13:
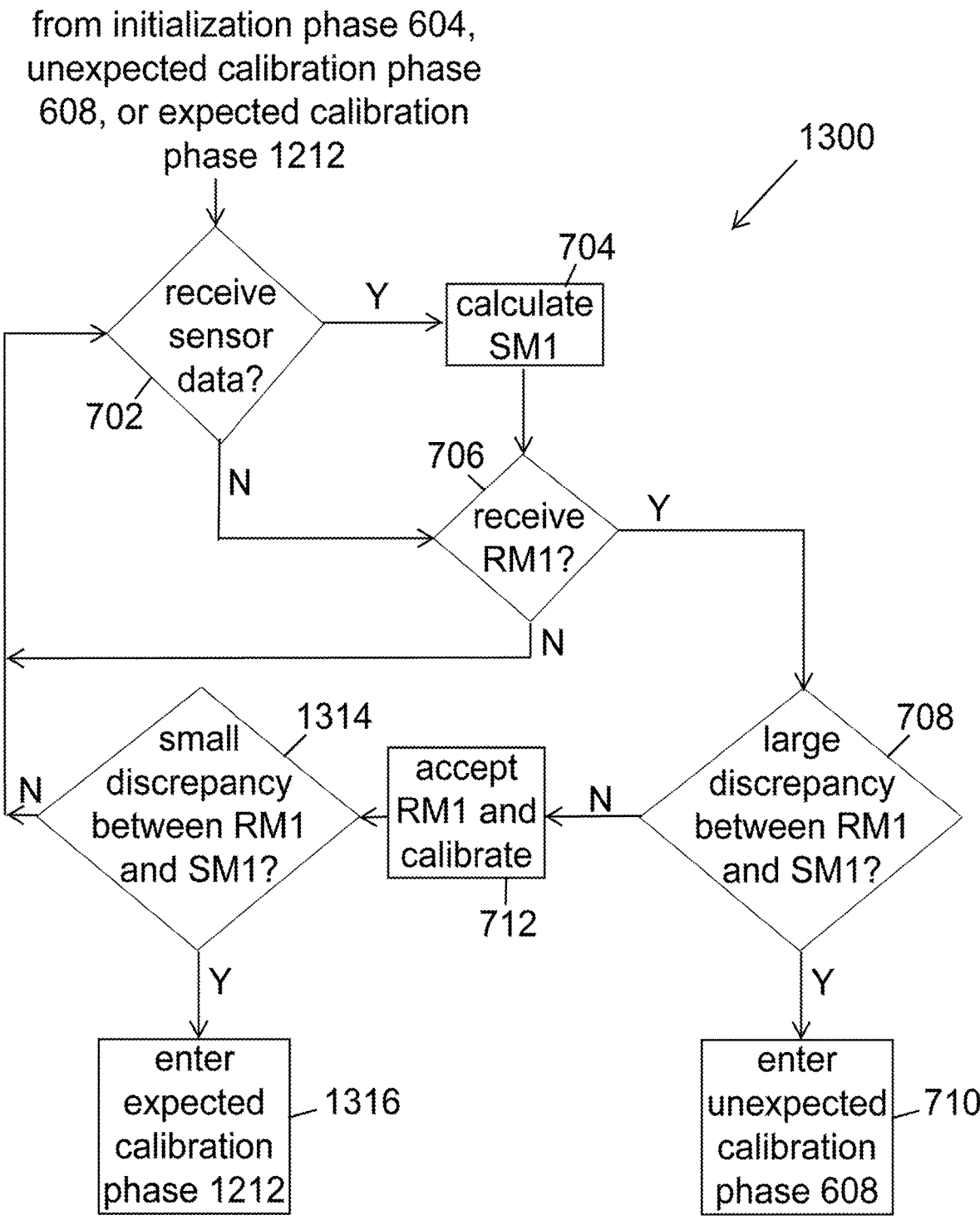
Figure 14:
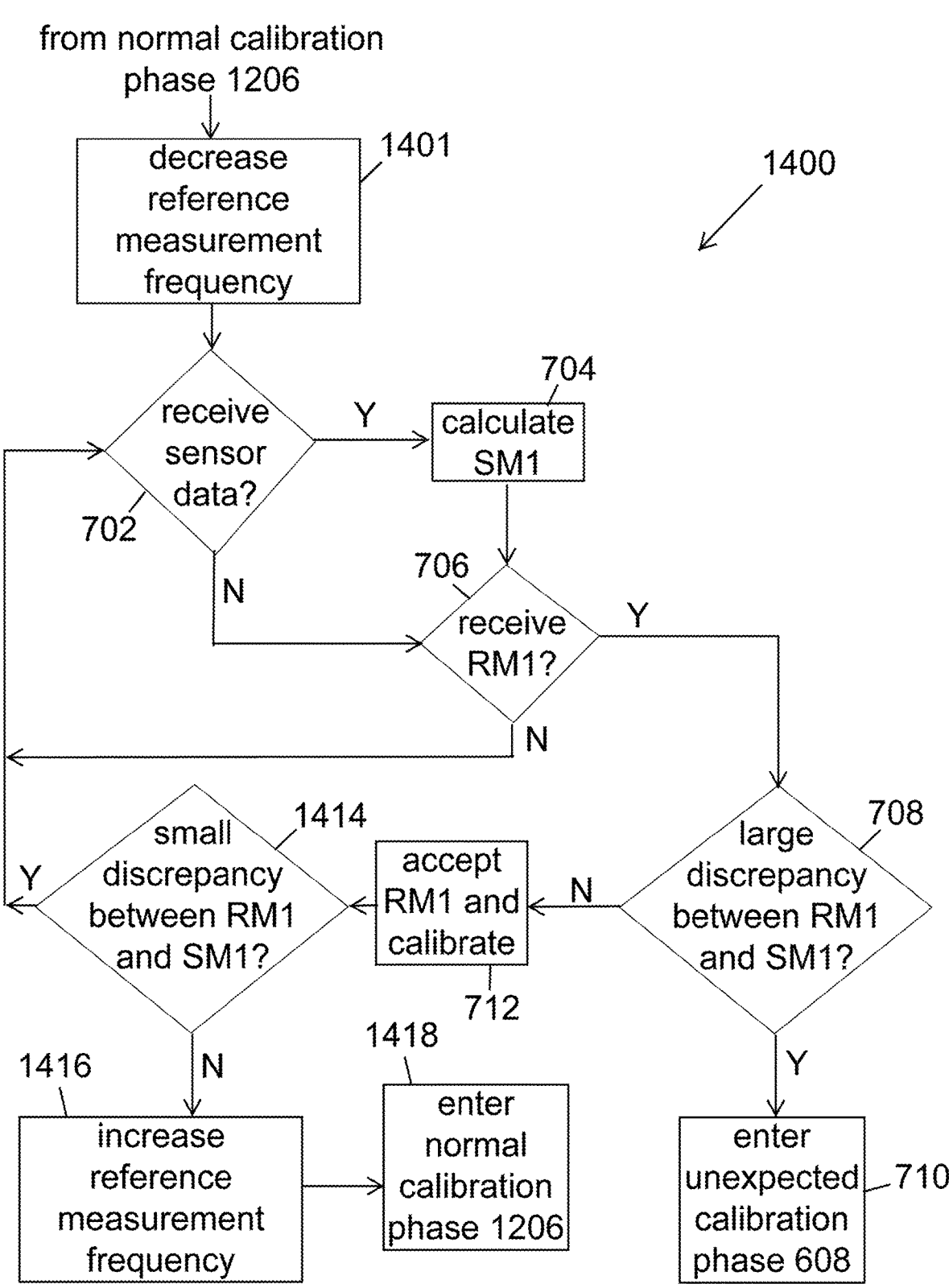

FIG. 13 is a flow chart illustrating an alternative normal calibration process embodying aspects of the present invention FIG. 14 is a flow chart illustrating an expected calibration process embodying aspects of the present invention.

DETAILED DESCRIPTION OF PREFERRED EMBODIMENTS

Figure 1:
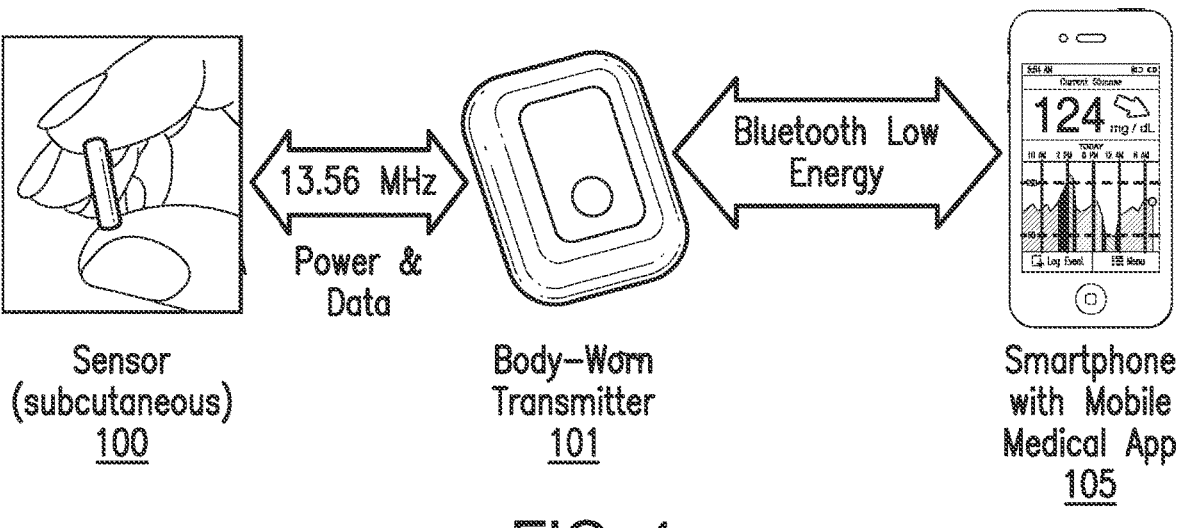
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transceiver 101, and a display device 105. In some embodiments, the sensor 100 may be small, fully subcutaneously implantable sensor measures analyte (e.g., glucose) concentrations in a medium (e.g., interstitial fluid) of a living animal (e.g., a living human). However, this is not required, and, in some alternative embodiments, the sensor 100 may be a partially implantable (e.g., transcutaneous) sensor or a fully external sensor. In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensor 100 via one or more wired connections. In some non-limiting embodiments, the transceiver 101 may be a smartphone (e.g., an NFC-enabled smartphone). In some embodiments, the transceiver 101 may communicate information (e.g., one or more analyte concentrations) wirelessly (e.g., via a Bluetooth™ communication standard such as, for example and without limitation Bluetooth Low Energy) to a hand held application running on a display device 105 (e.g., smartphone). In some embodiments, the analyte monitoring system 50 may include a web interface for plotting and sharing of uploaded data.

Figure 2:
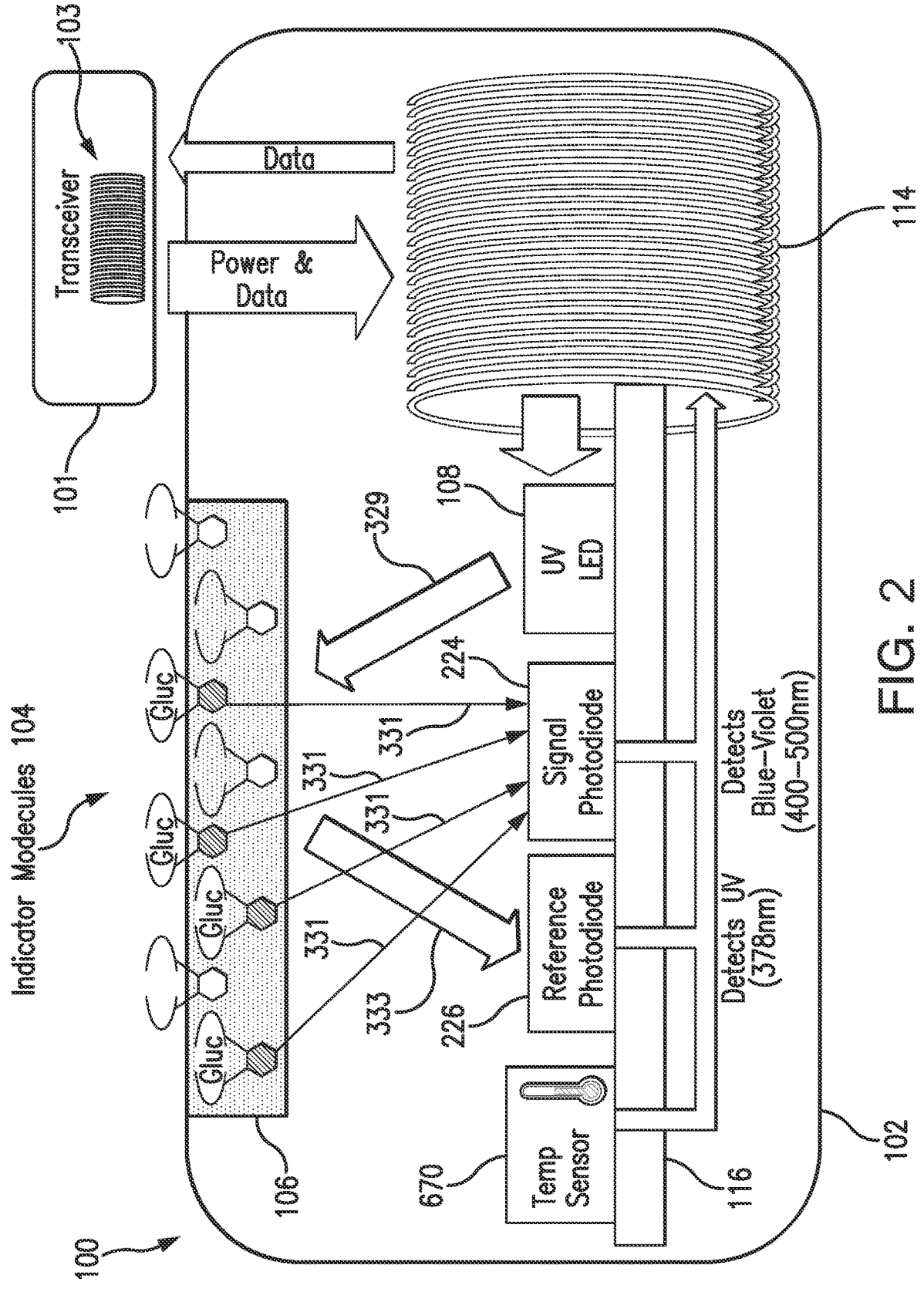
FIG. 2 is a schematic view illustrating a sensor and transceiver of an analyte monitoring system embodying aspects of the present invention.

In some embodiments, as illustrated in FIG. 2, the transceiver 101 may include an inductive element 103, such as, for example, a coil. The transceiver 101 may generate an electromagnetic wave or electrodynamic field (e.g., by using a coil) to induce a current in an inductive element 114 of the sensor 100, which powers the sensor 100. The transceiver 101 may also convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive sensor data (e.g., measurement information) from the sensor 100. For example, in a non-limiting embodiment, the transceiver 101 may receive sensor data by detecting modulations in the electromagnetic wave generated by the sensor 100, e.g., by detecting modulations in the current flowing through the coil 103 of the transceiver 101.

The inductive element 103 of the transceiver 101 and the inductive element 114 of the sensor 100 may be in any configuration that permits adequate field strength to be achieved when the two inductive elements are brought within adequate physical proximity.

In some non-limiting embodiments, as illustrated in FIG. 2, the sensor 100 may be encased in a sensor housing 102 (i.e., body, shell, capsule, or encasement), which may be rigid and biocompatible. The sensor 100 may include an analyte indicator element 106, such as, for example, a polymer graft coated, diffused, adhered, or embedded on or in at least a portion of the exterior surface of the sensor housing 102. The analyte indicator element 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator element 106. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator element 106 as reflection light 333. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670. In some non-limiting embodiments, the sensor 100 may include a drug-eluting polymer matrix that disperses one or more therapeutic agents (e.g., an anti-inflammatory drug).

In some embodiments, as illustrated in FIG. 2, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116 and/or a core (e.g., ferrite core) for the inductive element 114. In some embodiments, the semiconductor substrate 116 and/or a core may provide communication paths between the various secured components.

In some embodiments, the one or more of the sensor housing 102, analyte indicator element 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650, 016.

Although in some embodiments, as illustrated in FIG. 2, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, as illustrated in FIGS. 1 and 2, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the sensor 100 may include a transceiver interface device. In some embodiments where the sensor 100 includes an antenna (e.g., inductive element 114), the transceiver interface device may include the antenna (e.g., inductive element 114) of sensor 100. In some of the transcutaneous embodiments where there exists a wired connection between the sensor 100 and the transceiver 101, the transceiver interface device may include the wired connection.

Figure 3:
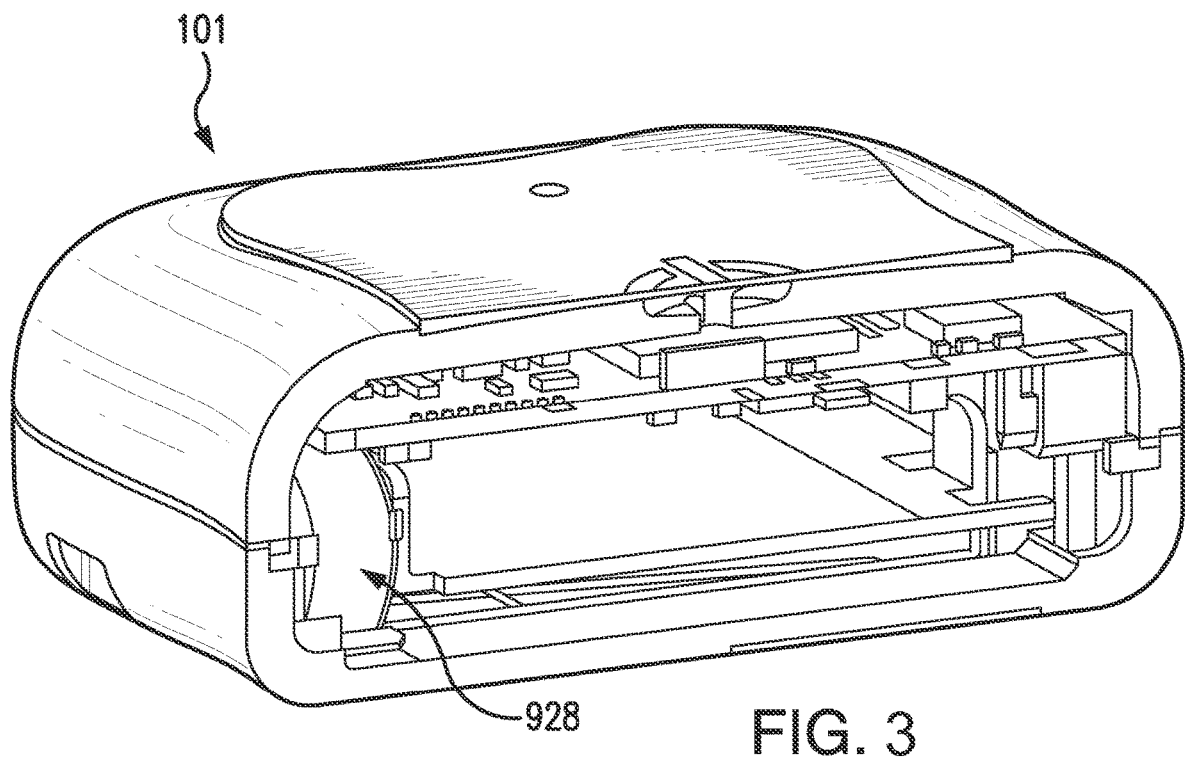
FIG. 3 is cross-sectional, perspective view of a transceiver embodying aspects of the invention.
Figure 4:
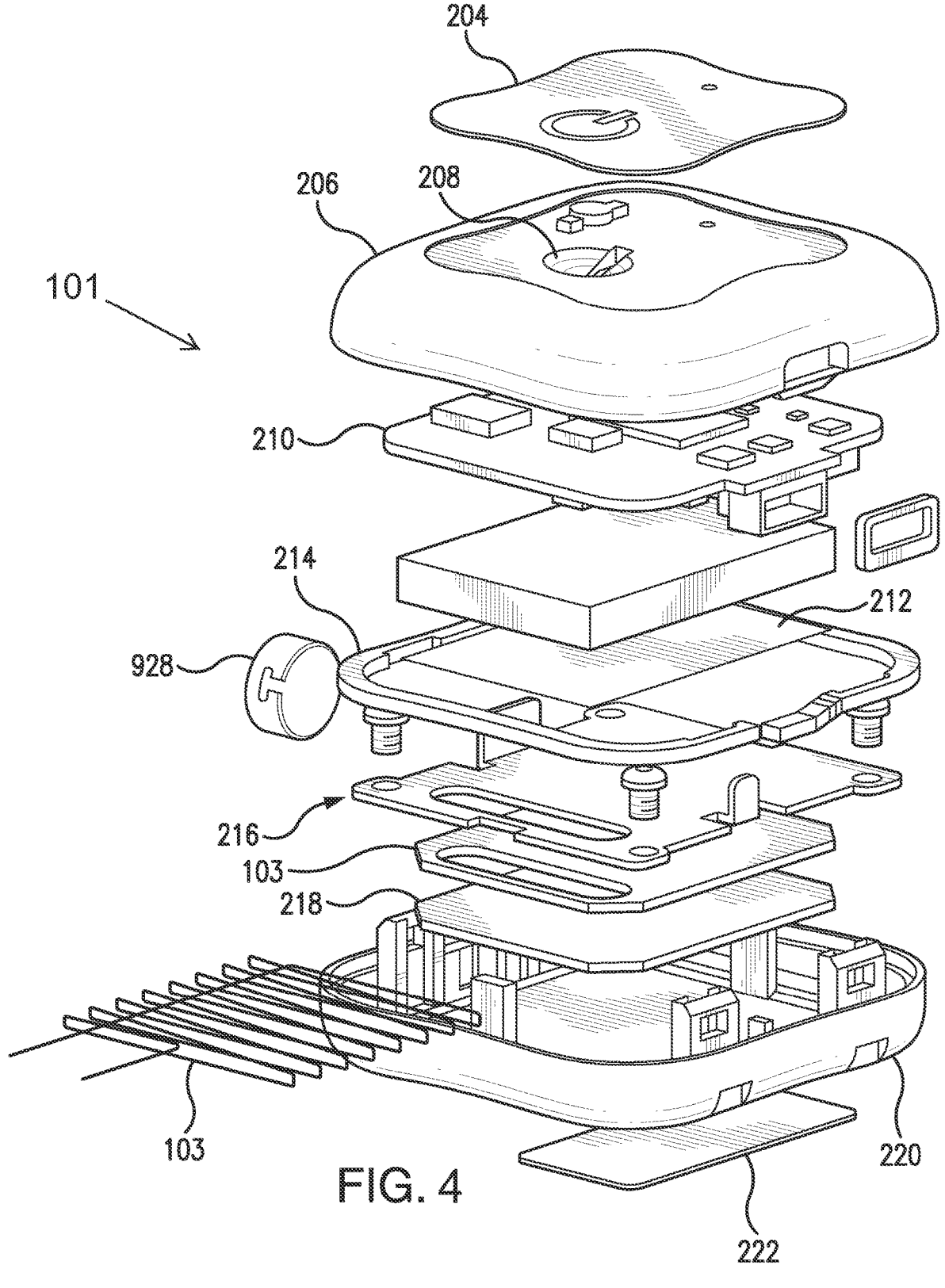
FIG. 4 is an exploded, perspective view of a transceiver embodying aspects of the invention.

FIGS. 3 and 4 are cross-sectional and exploded views, respectively, of a non-limiting embodiment of the transceiver 101, which may be included in the analyte monitoring system illustrated in FIG. 1. As illustrated in FIG. 4, in some non-limiting embodiments, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver 101 may be programmed and functionally tested. In some embodiments, assembled transceivers 101 may be packaged into their final shipping containers and be ready for sale.

In some embodiments, as illustrated in FIGS. 3 and 4, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the antenna 103 may be robust and capable of resisting various impacts. In some embodiments, the transceiver 101 may be suitable for placement, for example, on an abdomen area, upper-arm, wrist, or thigh of a patient body. In some non-limiting embodiments, the transceiver 101 may be suitable for attachment to a patient body by means of a biocompatible patch. Although, in some embodiments, the antenna 103 may be contained within the housing 206 and 220 of the transceiver 101, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 5:
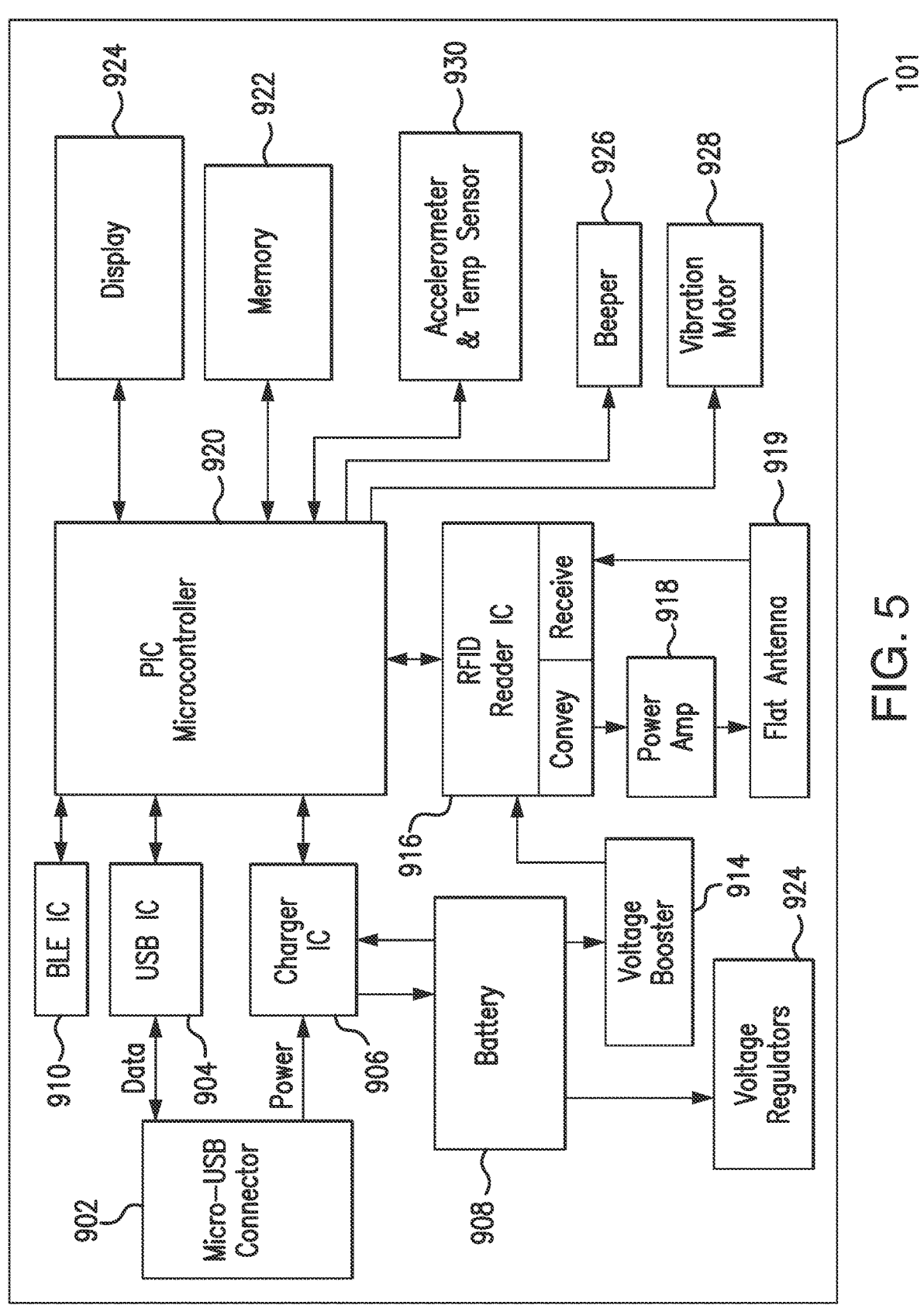
FIG. 5 is a schematic view illustrating a transceiver embodying aspects of the present invention.

FIG. 5 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer (e.g., personal computer 109) or a display device 105 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device

105 (e.g., a smartphone) and/or to receive power, which may be used, for example, to charge the battery 908.

In some embodiments, the transceiver 101 may have a wireless communication IC 910, which enables wireless communication with an external device, such as, for example, one or more personal computers (e.g., personal computer 109) or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a display interface device, which may enable communication by the transceiver 101 with one or more display devices 105. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductive element 103 is a flat antenna. In some non-limiting embodiments, the antenna may be flexible. However, as noted above, the inductive element 103 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 103 to the sensor 100.

The transceiver 101 may include a peripheral interface controller (PIC) microcontroller 920 and memory 922 (e.g., Flash memory), which may be non-volatile and/or capable of being electronically erased and/or rewritten. The PIC microcontroller 920 may control the overall operation of the transceiver 101. For example, the PIC microcontroller 920 may control the connector IC 904 or wireless communication IC 910 to transmit data via wired or wireless communication and/or control the RFID reader IC 916 to convey data via the inductive element 103. The PIC microcontroller 920 may also control processing of data received via the inductive element 103, connector 902, or wireless communication IC 910.

In some embodiments, the transceiver 101 may include a sensor interface device, which may enable communication by the transceiver 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, the transceiver 101 may include a display 924 (e.g., liquid crystal display and/or one or more light emitting diodes), which PIC microcontroller 920 may control to display data (e.g., analyte concentration values). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor, that may be used in the processing performed by the PIC microcontroller 920.

In some embodiments, the transceiver 101 may be a body-worn transceiver that is a rechargeable, external device worn over the sensor implantation or insertion site. The transceiver 101 may supply power to the proximate sensor 100, calculate analyte concentrations from data received from the sensor 100, and/or transmit the calculated analyte concentrations to a display device 105 (see FIG. 1). Power may be supplied to the sensor 100 through an inductive link (e.g., an inductive link of 13.56 MHz). In some embodiments, the transceiver 101 may be placed using an adhesive patch or a specially designed strap or belt. The external transceiver 101 may read measured analyte data from a subcutaneous sensor 100 (e.g., up to a depth of 2 cm or more). The transceiver 101 may periodically (e.g., every 2, 5, or 10 minutes) read sensor data and calculate an analyte concentration and an analyte concentration trend. From this information, the transceiver 101 may also determine if an alert and/or alarm condition exists, which may be signaled to the user (e.g., through vibration by vibration motor 928 and/or an LED of the transceiver's display 924 and/or a display of a display device 105). The information from the transceiver 101 (e.g., calculated analyte concentrations, calculated analyte concentration trends, alerts, alarms, and/or notifications) may be transmitted to a display device 105 (e.g., via Bluetooth Low Energy with Advanced Encryption Standard (AES)-Counter CBC-MAC (CCM) encryption) for display by a mobile medical application (MMA) being executed by the display device 105. In some non-limiting embodiments, the MMA may provide alarms, alerts, and/or notifications in addition to any alerts, alarms, and/or notifications received from the transceiver 101. In one embodiment, the MMA may be configured to provide push notifications. In some embodiments, the transceiver 101 may have a power button (e.g., button 208) to allow the user to turn the device on or off, reset the device, or check the remaining battery life. In some embodiments, the transceiver 101 may have a button, which may be the same button as a power button or an additional button, to suppress one or more user notification signals (e.g., vibration, visual, and/or audible) of the transceiver 101 generated by the transceiver 101 in response to detection of an alert or alarm condition.

In some embodiments, the transceiver 101 of the analyte monitoring system 50 may receive raw signals indicative of an amount or concentration of an analyte in proximity to the analyte indicator element 106 of the analyte sensor 100. In some embodiments, the transceiver 101 may receive the raw signals from the sensor 100 periodically (e.g., every 5, 10, or 20 minutes). In some embodiments, the raw signals may include one or more measurements (e.g., one or more measurements indicative of the level of emission light 331 from the indicator molecules 104 as measured by the photodetector 224, one or more measurements indicative of the level of reference light 333 as measured by photodetector 226, and/or one or more temperature measurements as measured by the temperature transducer 670). In some embodiments, the transceiver 101 may use the received raw signals to calculate analyte concentration. In some embodiments, the transceiver 100 may store one or more calculated analyte concentrations (e.g., in memory 922). In some embodiments, the transceiver 100 may convey one or more calculated analyte concentrations to the display device 105, and the display device 105 may display the one or more calculated analyte concentrations.

In some embodiments, the analyte monitoring system 50 may calibrate the conversion of raw signals to analyte concentration. In some embodiments, the calibration may be performed approximately periodically (e.g., approximately every 12 or 24 hours). In some embodiments, the calibration may be performed using one or more reference measurements (e.g., one or more self-monitoring blood glucose (SMBG) measurements), which may be entered into the analyte monitoring system 50 using the user interface of the display device 105. In some embodiments, the transceiver 101 may receive the one or more reference measurements from the display device 105 and perform the calibration. One or more of the reference measurements may be erroneous and may lead to erroneous analyte measurement calculation if used as a calibration point for the calibrating of the conversion of raw sensor data to analyte measurements. Accordingly, the analyte monitoring system 5 (e.g., the transceiver 101) may determine whether to accept (or reject) reference measurements as calibration points in the calibration process. This calibration point acceptance process may be used to prevent erroneous reference measurements from being used as calibration points when calibrating the function used to convert raw sensor data (e.g., light and/or temperature measurements) into analyte measurements (e.g., analyte concentrations). In this way, the calibration point acceptance process may increase the accuracy and/or precision of the analyte measurements.

Figure 6:
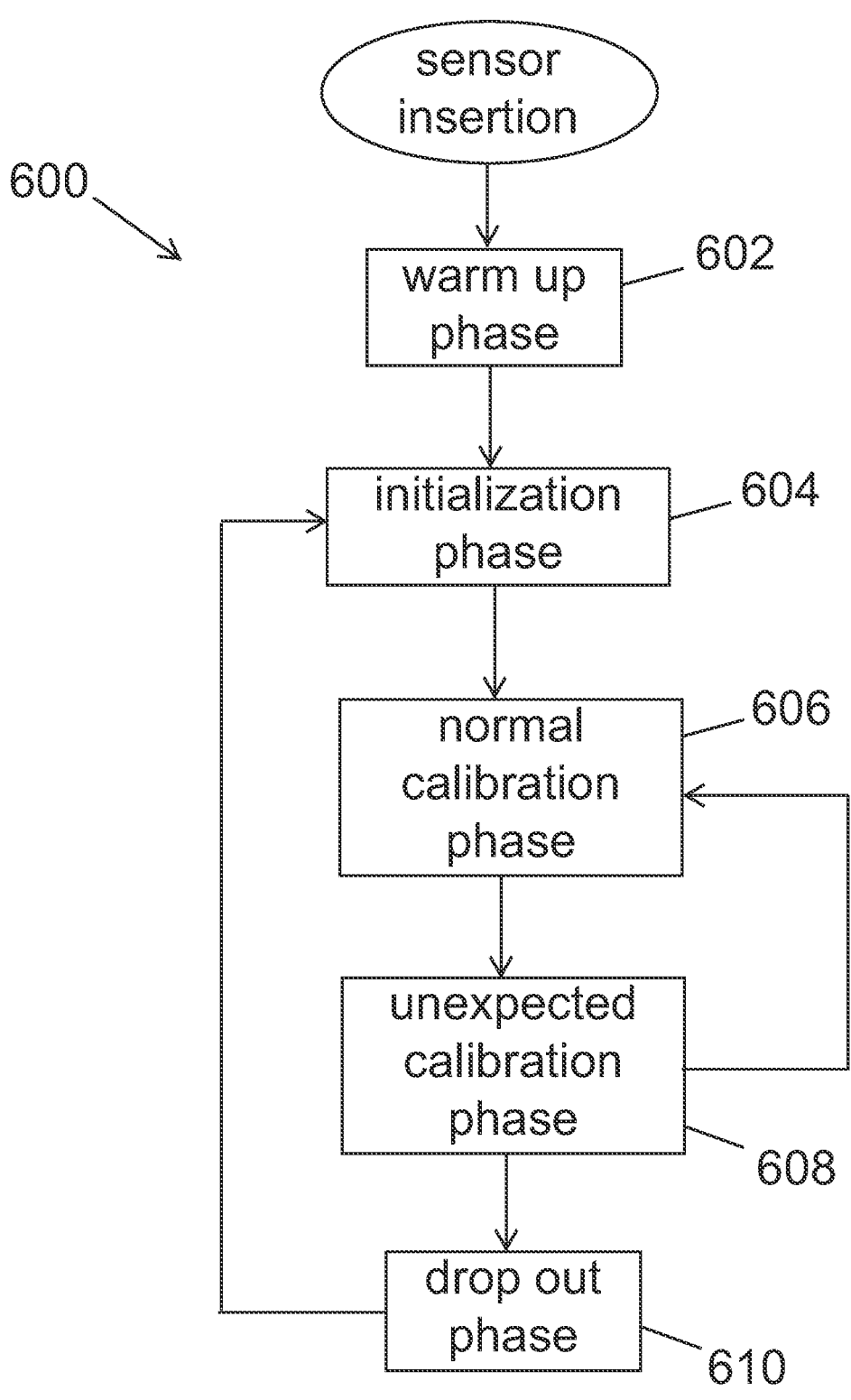
FIG. 6 is a flow chart illustrating a process for controlling initialization and calibration of an analyte monitoring system embodying aspects of the present invention.

FIG. 6 is a flow chart illustrating a process 600 for controlling initialization and calibration of an analyte monitoring system 50. In some embodiments, the transceiver 101 may perform one or more steps of the control process 600. In some non-limiting embodiments, the PIC microcontroller 920 of the transceiver 101 may perform one or more steps of the control process 600. In some embodiments, the process 600 may begin after insertion or implantation of the analyte sensor 100.

In some embodiments, the process 600 may begin with a warm up phase 602 in which the transceiver 101 allows the sensor 100 to adjust to being fully or partially in the body. In some non-limiting embodiments, the warm up phase 602 may give the analyte indicator element 106 time to hydrate. In some non-limiting embodiments, the transceiver 101 stays in the warm up phase 602 for a predetermined period of time such as, for example and without limitation, 12 or 24 hours. However, this is not required, and, in some alternative embodiments, the transceiver 101 may monitor sensor conditions during the warm up phase 602 and exit the warm up phase 602 after the sensor conditions have stabilized. In some embodiments, after completion of the warm up phase 602, the process 600 may proceed to an initialization phase 604. In some alternative embodiments, the warm up phase 602 may not be necessary (e.g., when the analyte sensor 100 is an external sensor or does not need time to acclimate to being inside the body). In these alternative embodiments, the process 600 may begin in an initialization step 604.

In some embodiments, in the initialization phase 604, the transceiver 101 may receive sensor data. In some non-limiting embodiments, the transceiver 101 may receive the sensor data periodically (e.g., every 2, 5, or 10 minutes). In some embodiments, in the initialization phase 604, the transceiver 101 may receive one or more reference measurements. In some non-limiting embodiments, the transceiver 101 may receive three or more reference measurements in the initialization phase 604. In some non-limiting embodiments, the transceiver 101 may receive the reference measurements periodically (e.g., approximately every 6 hours). In some embodiments, the transceiver 101 may store the reference measurements in a calibration point memory, which may be, for example and without limitation, a circular buffer. In some embodiments, the transceiver 101 may use the one or more reference measurements as calibration points to perform an initial calibration of the conversion function used to calculate analyte measurements from the sensor data. In some embodiments, the transceiver 101 may receive the one or more reference measurements from the display device 105. In some non-limiting embodiments, the transceiver 101 may cause the display device 105 to prompt a user for the one or more reference measurements, and, in response, the user may enter the one or more reference measurements into the display device 105.

In some non-limiting embodiments, during the initialization phase 604, no analyte measurements are displayed to the user. In some embodiments, after the completion of the initialization phase 604, the process 600 may proceed to a normal calibration phase 606. In some embodiments, the normal calibration phase 606 may be a steady state phase. In some non-limiting embodiments, although not shown in FIG. 6, if the transceiver 101 determines that one or more references measurements received during the initialization phase 604 are unexpected, the process 600 may proceed from the initialization phase 604 to an unexpected calibration phase 608 (instead of proceeding to the normal calibration phase 606).

In some embodiments, in the normal calibration phase 606, the transceiver 101 may receive sensor data and calculate analyte measurements using the conversion function and the received sensor data. In some non-limiting embodiments, the transceiver 101 may receive the sensor data periodically (e.g., every 2, 5, or 10 minutes). In some embodiments, the transceiver 101 may display one or more analyte measurements. In some non-limiting embodiments, in the normal calibration phase 606, the transceiver 101 may display the one or more analyte measurements by transmitting them to the display device 105 for display.

In some embodiments, in the normal calibration phase 606, the transceiver 101 may receive one or more reference measurements. In some non-limiting embodiments, the transceiver 101 may receive the reference measurements periodically (e.g., approximately every 12 hours). In some non-limiting embodiments, the transceiver 101 may receive the reference measurements less frequently than in the initialization phase 604. However, this is not required. It is also not required that the transceiver 101 receive reference measurements periodically, and, in some alternative embodiments, the transceiver 101 may receive reference measurements on an as-needed basis (e.g., as determined by the transceiver 101 by analyzing the sensor data). In some embodiments, the transceiver 101 may receive the reference measurements from the display device 105. In some non-limiting embodiments, in the normal calibration phase 606, the transceiver 101 may cause the display device 105 to prompt a user for the one or more reference measurements, and, in response, the user may enter the one or more reference measurements into the display device 105.

In some embodiments, in the normal calibration phase 606, the transceiver 101 may determine whether to accept the reference measurement or to treat the reference measurement as unexpected. In some non-limiting embodiments, the transceiver 101 may determine whether to accept a received reference measurement by comparing the reference measurement to the most-recent sensor measurement (i.e., the most-recent analyte measurement calculated by the conversion function using received sensor data). In some embodiments, if the transceiver 101 determines that the reference measurement is acceptable, the transceiver 101 may calibrate (or re-calibrate or update) the conversion function using the reference point as a calibration point. In some embodiments, if the transceiver 101 determines that a reference measurement is unexpected, the process 600 may proceed to an unexpected calibration phase 608.

In some embodiments, during the unexpected calibration phase 608, the transceiver 101 may receive a new reference measurement. In some embodiments, the transceiver 101 may use the new reference measurement to determine whether one or both of the unexpected reference measurement and the conversion function, which was used to calculate the sensor measurement to which the unexpected reference measurement was compared, were erroneous. If the transceiver 101 determines that only the unexpected measurement was erroneous, the transceiver 101 may reject the unexpected measurement, accept the new reference measurement as a calibration point, and perform a calibration of the conversion function. If the transceiver 101 determines that only the conversion function was erroneous, the transceiver 101 may accept both the unexpected and new reference measurements as calibration points and perform a calibration of the calibration function. If the transceiver 101 accepts one or more of the reference measurements, the process 600 may proceed back to the normal calibration phase 606. Otherwise, the transceiver 101 may try again with another new reference measurement, or the process 600 may proceed to a sensor dropout phase 610.

In some embodiments, in the sensor dropout phase 610, the transceiver 101 may receive sensor data from the sensor 100, but no analyte measurements are displayed to the user. In some embodiments, the process 600 may remain in the dropout phase 610 for a period of time (e.g., at least six hours) before proceeding back to the initialization phase 604. However, the sensor dropout phase 610 is not necessary, and, in some alternative embodiments, the process 600 may proceed directly to the initialization phase 604 from the unexpected calibration phase 608.

Figure 7:
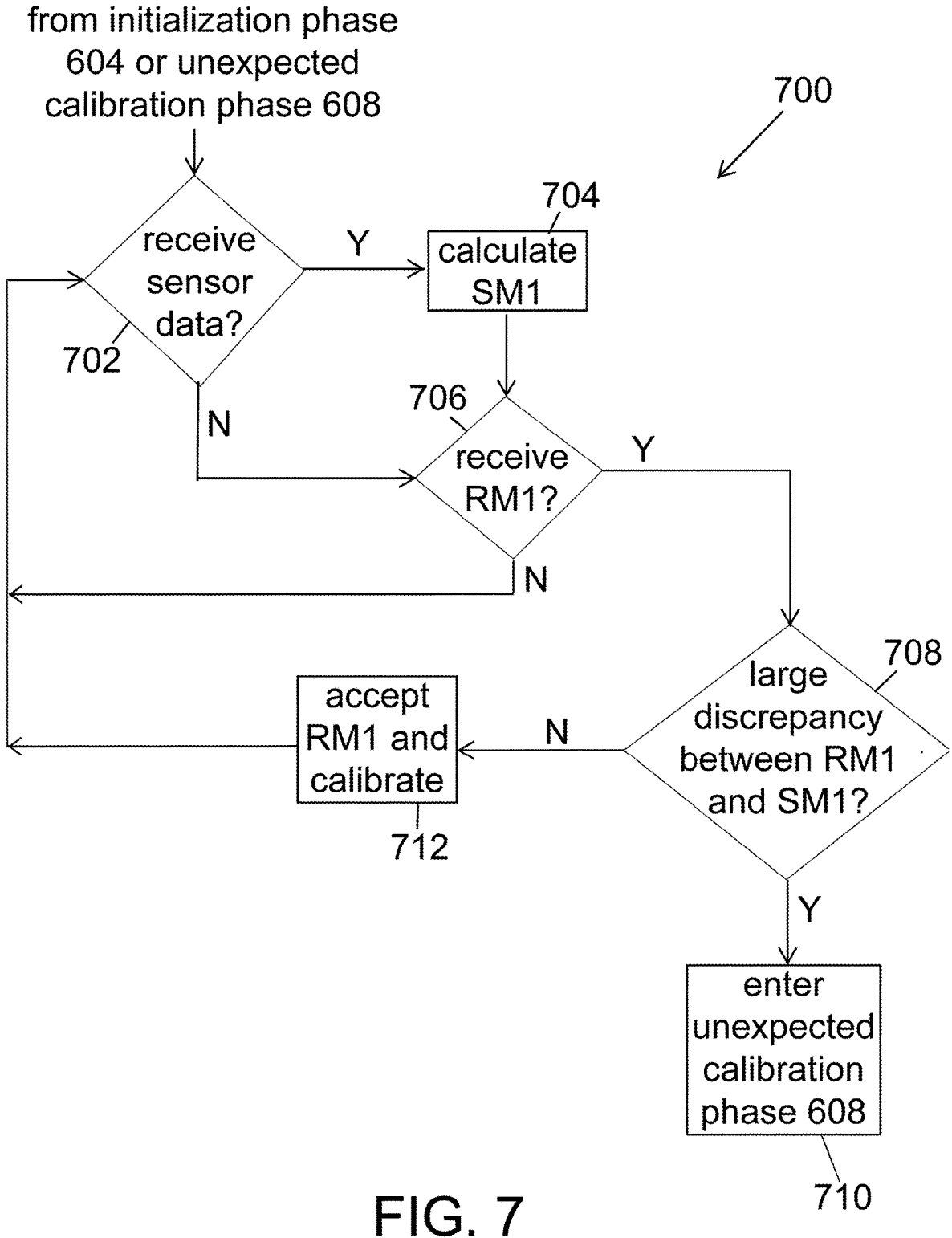
FIG. 7 is a flow chart illustrating a normal calibration process embodying aspects of the present invention.

FIG. 7 is a flow chart illustrating a normal calibration process 700, which may be performed during the normal calibration phase 606 of the control process 600 illustrated in FIG. 6. In some embodiments, the transceiver 101 may perform one or more steps of the normal calibration process 700. In some non-limiting embodiments, the PIC microcontroller 920 of the transceiver 101 may perform one or more steps of the normal calibration process 700.

In some embodiments, the normal calibration process 700 may include a step 702 in which the transceiver 101 determines whether the transceiver 101 has received sensor data (e.g., light and/or temperature measurements) from the sensor 100. In some embodiments, the sensor data may be received following a command (e.g., a measurement command or a read sensor data command) conveyed from the transceiver 101 to the sensor 100. However, this is not required, and, in some alternative embodiments, the sensor 100 may control when sensor data is conveyed to the transceiver 101, or the sensor 100 may continuously convey sensor data to the transceiver 101. In some non-limiting embodiments, the transceiver 101 may receive the sensor data periodically (e.g., every 2, 5, or 10 minutes). In some embodiments, the transceiver 101 may receive the sensor data wirelessly. For example and without limitation, in some non-limiting embodiments, the transceiver 101 may receive the sensor data by detecting modulations in an electromagnetic wave generated by the sensor 100, e.g., by detecting modulations in the current flowing through the coil 103 of the transceiver 101. However, this is not required, and, in some alternative embodiments, the transceiver 101 may receive the sensor data via a wired connection to the sensor 100. In some non-limiting embodiments, if the sensor has received sensor data, the normal calibration process 700 may proceed from step 702 to a measurement calculation step 704. In some non-limiting embodiments, if the transceiver 101 has not received sensor data, the normal calibration process 700 may proceed from step 702 to a step 706.

In some non-limiting embodiments, the normal calibration process 700 may include the measurement calculation step 704. In some embodiments, the step 704 may include calculating a sensor measurement SM1 using the current calibration function and the received sensor data. In some embodiments, the sensor measurement SM1 may be a measurement of the amount or concentration of the analyte in proximity to the analyte indicator element 106. In some embodiments, in step 704, the transceiver 101 may display the calculated sensor measurement SM1. In some non-limiting embodiments, the transceiver 101 may display the sensor measurement SM1 by transmitting it to the display device 105 for display.

In some non-limiting embodiments, the normal calibration process 700 may include the step 706 in which the transceiver 101 determines whether the transceiver 101 has received a reference measurement RM1. The reference measurement RM1 may be, for example and without limitation, an SMBG measurement obtained from, for example and without limitation, a finger-stick blood sample. In some embodiments, the transceiver 101 may receive reference measurements periodically or on an as-needed basis. In some embodiments, the transceiver 101 may receive the reference measurement RM1 from the display device 105. In some non-limiting embodiments, the transceiver 101 may cause the display device 105 to prompt a user for the reference measurement RM1, and, in response, the user may enter the reference measurement RM1 into the display device 105. If the transceiver 101 has not received a reference measurement RM1, the normal calibration process 700 may proceed back to step 702 and continue using the current calibration function to calculate sensor measurements when sensor data is received until a reference measurement RM1 is received. If the transceiver 101 has received a reference measurement RM1, the normal calibration process 700 may proceed to a step 708.

In some non-limiting embodiments, the normal calibration process 700 may include the step 708 in which the transceiver 101 determines whether to accept the reference measurement RM1 or to treat the reference measurement RM1 as unexpected. In some non-limiting embodiments, the step 708 may include comparing the reference measurement RM1 and the most-recent sensor measurement SM1 (i.e., the most-recent analyte measurement calculated by the conversion function using received sensor data). In some embodiments, the most-recent sensor measurement SM1 may have been calculated within a certain amount of time, such as, for example and without limitation, 5, 10, or 20 minutes. In some non-limiting embodiments, the step 708 may include determining whether there is a large discrepancy between the reference measurement RM1 and the most-recent sensor measurement SM1. In some non-limiting embodiments, the transceiver 101 may determine that a reference measurement RM1 is unexpected if there is a large discrepancy between the reference measurement RM1 and the most-recent sensor measurement SM1. In non-limiting some embodiments, the transceiver 101 may determine that the reference measurement is acceptable if the difference between the reference measurement RM1 and the sensor measurement SM1 is within a threshold amount. In some non-limiting embodiments, the threshold amount may be a percentage of the sensor measurement SM1 (e.g., ±30% of SM1) or a deviation of the sensor measurement SM1 (e.g., ±10 mg/dL of SM1).

In some non-limiting embodiments, the threshold amount may be a fixed threshold. However, this is not required, and, in some alternative embodiments, the threshold amount may vary. In some non-limiting alternative embodiments, the threshold amount may vary based on one or more of the sensor measurement SM1 and the reference measurement RM1. In some non-limiting embodiments where the threshold amount varies based on reference amount RM1, the reference measurement range may be divided into two or more sub-ranges, and the transceiver 101 may use a different threshold for each of the sub-ranges. That is, in some non-limiting embodiments, if the reference measurement RM1 falls into a second reference measurement sub-range, the transceiver 101 may use a second threshold when determining whether the reference measurement RM1 is acceptable. For example and without limitation, in one non-limiting alternative embodiment where the threshold amount varies based on reference measurement sub-ranges, the reference measurement range may be divided into the following five sub-ranges: (i) less than 70 mg/dL, (ii) greater than or equal to 70 mg/dL and less than 140 mg/dL, (iii) greater than or equal to 140 mg/dL and less than 180 mg/dL, (iv) greater than or equal to 180 mg/dL and less than 240 mg/dL, and (v) greater than or equal to 240 mg/dL, and the transceiver 101 may use a different threshold amount for each of the five sub-ranges. However, this is not required, and some alternative embodiments may use different sub-ranges and/or a different number of sub-ranges. In some other alternative embodiments having a varying threshold amount, the transceiver 101 may use a linear or non-linear formula to calculate the threshold amount that should be used for a particular reference measurement RM1 or sensor measurement SM1.

In some embodiments, if the transceiver 101 determines that the reference measurement RM1 is unexpected, the normal calibration process 700 may proceed from step 708 to a step 710 in which the transceiver 101 leaves the normal calibration phase and enters an unexpected calibration phase (e.g., the unexpected calibration phase 608 of FIG. 6). In some embodiments, if the transceiver 101 determines that the reference measurement RM1 is acceptable, the normal calibration process 700 may proceed from step 708 to a step 712.

In some embodiments, in step 712, the transceiver 101 may accept the reference measurement RM1 as a calibration point. In some non-limiting embodiments, accepting the reference measurement RM1 as a calibration point may include storing the reference measurement RM1 in a calibration point memory (e.g., a circular buffer). In some embodiments, in step 712, the transceiver 101 may calibrate the conversion function used to calculate analyte measurements from sensor data. In some non-limiting embodiments, the transceiver 101 may calibrate the conversion function using one or more of the calibration points stored in the calibration point memory. In some embodiments, the one or more calibration points used to calibrate the conversion function may include the reference measurement RM1. In some non-limiting embodiments, the transceiver 101 may assign weights to the one or more calibration points. In some non-limiting embodiments, the transceiver 101 may assign weights based on the age of the calibration points with less weight being given to older calibration points. In some embodiments, the normal calibration process 700 may proceed from step 712 to step 702, and the transceiver 101 may use the updated conversion function to calculate sensor measurements from subsequent sensor data.

Figure 8:
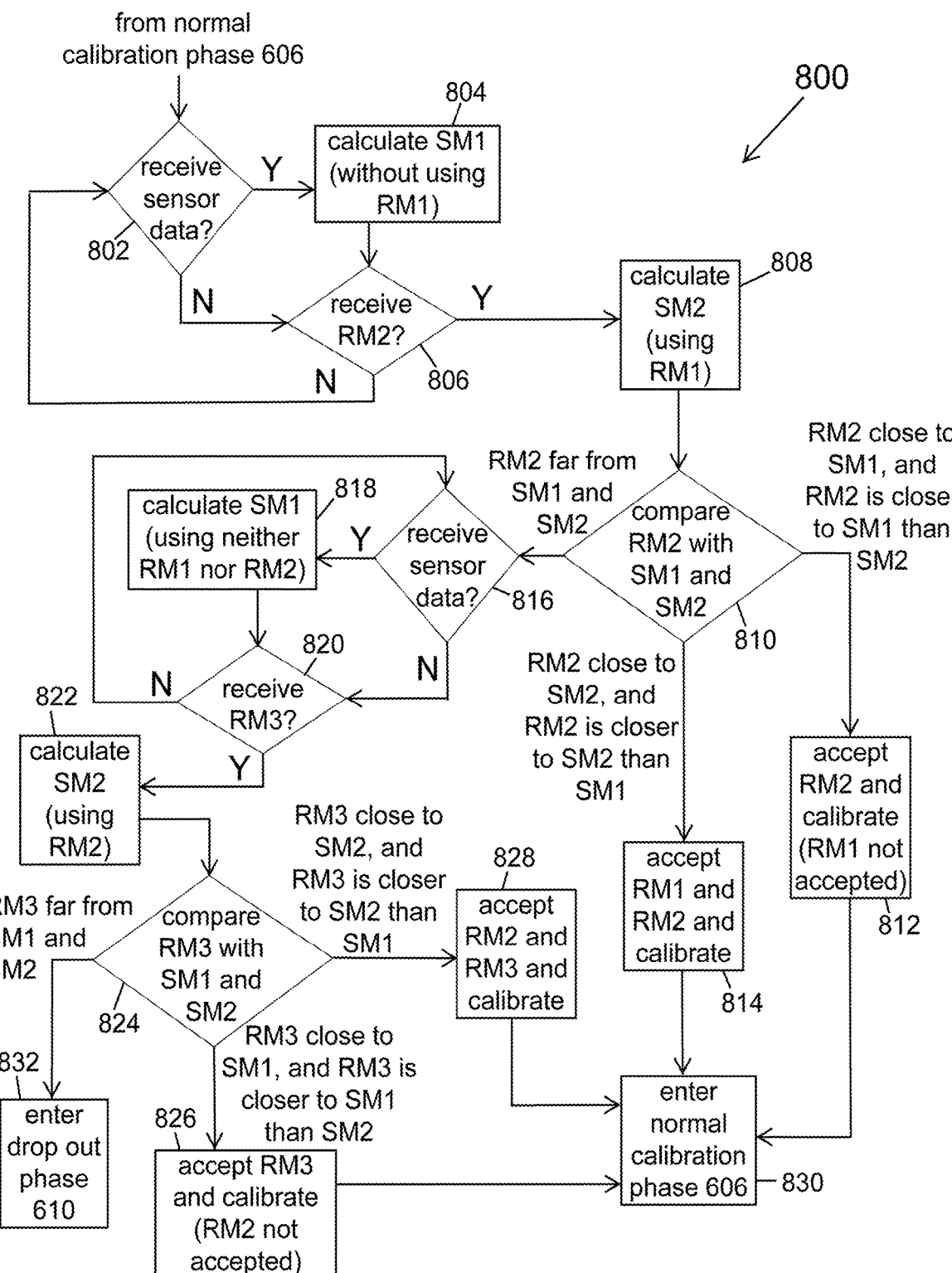
FIG. 8 is a flow chart illustrating an unexpected calibration process embodying aspects of the present invention.

FIG. 8 is a flow chart illustrating an unexpected calibration process 800, which may be performed during the unexpected calibration phase 608 of the control process 600 illustrated in FIG. 6. In some embodiments, the transceiver 101 may perform one or more steps of the unexpected calibration process 800. In some non-limiting embodiments, the PIC microcontroller 920 of the transceiver 101 may perform one or more steps of the unexpected calibration process 800.

In some embodiments, the unexpected calibration process 800 may include a step 802 in which the transceiver 101 determines whether the transceiver 101 has received sensor data (e.g., light and/or temperature measurements) from the sensor 100. In some non-limiting embodiments, if the sensor has received sensor data, the unexpected calibration process 800 may proceed from step 802 to a measurement calculation step 804. In some non-limiting embodiments, if the transceiver 101 has not received sensor data, the unexpected calibration process 800 may proceed from step 802 to a step 806.

In some non-limiting embodiments, the unexpected calibration process 800 may include the measurement calculation step 804. In some embodiments, the step 804 may include calculating a sensor measurement SM1 using the current calibration function, which does not take the reference measurement RM1 into account, and the received sensor data. In some embodiments, in step 804, the transceiver 101 may display the calculated sensor measurement SM1. In some non-limiting embodiments, the transceiver 101 may display the sensor measurement SM1 by transmitting it to the display device 105 for display.

In some embodiments, the unexpected calibration process 800 may include a step 806 in which the transceiver 101 determines whether the transceiver 101 has received a reference measurement RM2. The reference measurement RM2 may be, for example and without limitation, an SMBG measurement obtained from, for example and without limitation, a finger-stick blood sample. In some non-limiting embodiments, the transceiver 101 may receive the reference measurement RM2 at least a period of time (e.g., 1 minute, 5 minutes, 10 minutes, 15 minutes, 30 minutes, 1 hour, etc.)

after receiving the unexpected reference measurement RM1. In some embodiments, the transceiver 101 may receive the reference measurement RM2 from the display device 105. In some non-limiting embodiments, after the period of time has passed since the unexpected reference measurement RM1 was received, the transceiver 101 may cause the display device 105 to prompt a user for the reference measurement RM2, and, in response, the user may enter the reference measurement RM2 into the display device 105. If the transceiver 101 has not received a reference measurement RM2, the unexpected calibration process 800 may proceed back to step 802 and continue using the current calibration function, which does not take the reference measurement RM1 into account, to calculate sensor measurements from sensor data until a reference measurement RM2 is received. If the transceiver 101 has received a reference measurement RM2, the unexpected calibration process 800 may proceed to a step 808.

In some embodiments, the unexpected calibration process 800 may include a step 808 in which the transceiver 101 calculates a sensor measurement SM2 using a conversion function that takes the unexpected reference measurement RM1 into account as a calibration point. In some non-limiting embodiments, in step 808, the transceiver 101 may additionally calculate a sensor measurement SM1 using a conversion function that does not take the unexpected reference measurement RM1 into account as a calibration point.

In some embodiments, the unexpected calibration process 800 may include a step 810 in which the transceiver 101 determines whether one or more of the reference measurements RM1 and RM2 are acceptable. In some non-limiting embodiments, the step 810 may include comparing the reference measurement RM2 with the most-recent sensor measurement SM1, which was calculated by a conversion function that did not take the unexpected reference measurement RM1 into account, and with the sensor measurement SM2, which was calculated by a conversion function that did take the unexpected reference measurement RM1 into account.

In some non-limiting embodiments, the step 810 may include determining whether there is a large discrepancy between the reference measurement RM2 and one or more of the sensor measurements SM1 and SM2. In non-limiting some embodiments, the transceiver 101 may determine whether the difference between the reference measurement RM2 and the sensor measurement SM1 is within a threshold amount and whether the difference between the reference measurement RM2 and the sensor measurement SM2 is within the threshold amount. In some non-limiting embodiments, the threshold amount may be a percentage of or deviation from sensor measurement SM1. In some non-limiting embodiments, the threshold amount may be a fixed, or the threshold amount may vary (e.g., based on the reference measurement RM2, sensor measurement SM1, or sensor measurement SM2). In some non-limiting embodiments, the step 810 may include determining whether the reference measurement RM2 is closer to the sensor measurement SM1 or sensor measurement SM2.

In some embodiments, in step 810, the transceiver 101 may determine that reference measurement RM2 is acceptable if the transceiver 101 determines both that (i) the difference between the reference measurement RM2 and the sensor measurement SM1, which was calculated without taking the unexpected reference measurement RM1 into account, is within the threshold amount and (ii) the reference measurement RM2 is closer to the sensor measurement SM1 than the sensor measurement SM2, which was calculated taking the unexpected reference measurement RM1 into account. However, this is not required, and, in some alternative embodiments, the transceiver 101 may determine that the reference measurement RM2 is acceptable in a different way. For example and without limitation, in one alternative embodiment, the transceiver 101 may determine that the reference measurement RM2 is acceptable if only one of conditions (i) and (ii) is met.

In some embodiments, in step 810, the transceiver 101 may determine that both reference measurements RM1 and RM2 are acceptable if the transceiver 101 determines both that (i) the difference between the reference measurement RM2 and the sensor measurement SM2, which was calculated taking the unexpected reference measurement RM1 into account, is within the threshold amount and (ii) the reference measurement RM2 is closer to the sensor measurement SM2 than the sensor measurement SM1, which was calculated without taking the unexpected reference measurement RM1 into account. However, this is not required, and, in some alternative embodiments, the transceiver 101 may determine that both reference measurements RM1 and RM2 are acceptable in a different way. For example and without limitation, in one alternative embodiment, the transceiver 101 may determine that the reference measurements RM1 and RM2 are acceptable if only one of conditions (i) and (ii) is met.

In some embodiments, in step 810, the transceiver 101 may be unable to determine that at least one of reference measurements RM1 and RM2 is acceptable if the difference between the reference measurement RM2 and the sensor measurement SM1 is outside the threshold amount and the difference between the reference measurement RM2 and the sensor measurement SM2 is outside the threshold amount.

In some embodiments, if the transceiver 101 determines in step 810 that the reference measurement RM2 is acceptable and that the reference measurement RM1 is not acceptable, the unexpected calibration process 800 may proceed from step 810 to a step 812 in which the transceiver 101 may accept only the reference measurement RM2 (and not the reference measurement RM1) as a calibration point. In some non-limiting embodiments, accepting the reference measurement RM2 as a calibration point may include storing the reference measurement RM2 in a calibration point memory (e.g., a circular buffer). In some embodiments, in step 812, the transceiver 101 may calibrate the conversion function used to calculate analyte measurements from sensor data. In some non-limiting embodiments, the transceiver 101 may calibrate the conversion function using one or more of the calibration points stored in the calibration point memory. In some embodiments, the one or more calibration points used to calibrate the conversion function may include the reference measurement RM2. In some embodiments, the unexpected calibration process 800 may proceed from step 812 to a step 830 in which the transceiver 101 leaves the unexpected calibration phase and enters a normal calibration phase (e.g., the normal calibration phase 606 of FIG. 6). In the normal calibration phase, the transceiver 101 may use the updated conversion function to calculate sensor measurements from subsequent sensor data.

In some embodiments, if the transceiver 101 determines in step 810 that both reference measurements RM1 and RM2 are acceptable, the unexpected calibration process 800 may proceed from step 810 to a step 814 in which the transceiver 101 may accept the reference measurements RM1 and RM2 as calibration points. In some non-limiting embodiments, accepting the reference measurements RM1 and RM2 as calibration points may include storing the reference measurements RM1 and RM2 in the calibration point memory. In some embodiments, in step 814, the transceiver 101 may calibrate the conversion function used to calculate analyte measurements from sensor data. In some non-limiting embodiments, the transceiver 101 may calibrate the conversion function using one or more of the calibration points stored in the calibration point memory. In some embodiments, the one or more calibration points used to calibrate the conversion function may include the reference measurements RM1 and RM2. In some embodiments, the unexpected calibration process 800 may proceed from step 814 to a step 830 in which the transceiver 101 leaves the unexpected calibration phase and enters a normal calibration phase (e.g., the normal calibration phase 606 of FIG. 6). In the normal calibration phase, the transceiver 101 may use the updated conversion function to calculate sensor measurements from subsequent sensor data.

In some embodiments, if the transceiver 101 is unable to determine in step 810 that at least one of the reference measurements RM1 and RM2 is acceptable, the transceiver 101 may reject the reference measurement RM1, treat the reference measurement RM2 as unexpected, and try again one or more times to find one or more acceptable reference measurements using one or more additionally received reference measurements. For example, in some non-limiting embodiments, if the transceiver 101 is unable to determines in step 810 that at least one of the reference measurements RM1 and RM2 is acceptable, the unexpected calibration process 800 may proceed from step 810 to a step 816 in which the transceiver 101 determines whether the transceiver 101 has received sensor data (e.g., light and/or temperature measurements) from the sensor 100. In some non-limiting embodiments, if the sensor has received sensor data, the unexpected calibration process 800 may proceed from step 816 to a measurement calculation step 818. In some non-limiting embodiments, if the transceiver 101 has not received sensor data, the unexpected calibration process 800 may proceed from step 816 to a step 820.

In some non-limiting embodiments, the unexpected calibration process 800 may include the measurement calculation step 818. In some embodiments, the step 818 may include calculating a sensor measurement SM1 using the current calibration function, which takes neither the rejected reference measurement RM1 nor the unexpected reference measurement RM2 into account, and the received sensor data. In some embodiments, in step 818, the transceiver 101 may display the calculated sensor measurement SM1. In some non-limiting embodiments, the transceiver 101 may display the sensor measurement SM1 by transmitting it to the display device 105 for display.

In some embodiments, the unexpected calibration process 800 may include a step 820 in which the transceiver 101 determines whether the transceiver 101 has received a reference measurement RM3. The reference measurement RM3 may be, for example and without limitation, an SMBG measurement obtained from, for example and without limitation, a finger-stick blood sample. In some non-limiting embodiments, the transceiver 101 may receive the reference measurement RM3 at least a period of time (e.g., 1 minute, 5 minutes, 10 minutes, 15 minutes, 30 minutes, 1 hour, etc.) after receiving the unexpected reference measurement RM2. In some embodiments, the transceiver 101 may receive the reference measurement RM3 from the display device 105. In some non-limiting embodiments, after the period of time has passed since the unexpected reference measurement RM2 was received, the transceiver 101 may cause the display device 105 to prompt a user for the reference measurement RM3, and, in response, the user may enter the reference measurement RM3 into the display device 105. If the transceiver 101 has not received a reference measurement RM3, the unexpected calibration process 800 may proceed back to step 816 and continue using the current calibration function, which does not take the reference measurements RM1 and RM2 into account, to calculate sensor measurements from sensor data until a reference measurement RM3 is received. If the transceiver 101 has received a reference measurement RM3, the unexpected calibration process 800 may proceed from step 820 to a step 822.

In some embodiments, the unexpected calibration process 800 may include a step 822 in which the transceiver 101 calculates a sensor measurement SM2 using a conversion function that takes the unexpected reference measurement RM2 (but not the rejected reference measurement RM1) into account as a calibration point. In some non-limiting embodiments, in step 822, the transceiver 101 may additionally calculate a sensor measurement SM1 using a conversion function that takes into account neither of the reference measurements RM1 and RM2 as calibration points.

In some embodiments, the unexpected calibration process 800 may include a step 824 in which the transceiver 101 determines whether one or more of the reference measurements RM2 and RM3 are acceptable. In some non-limiting embodiments, the step 824 may include comparing the reference measurement RM3 with the most-recent sensor measurement SM1, which was calculated by a conversion function that did not take the unexpected reference measurement RM2 into account, and with the sensor measurement SM2, which was calculated by a conversion function that did take the unexpected reference measurement RM2 into account.

In some non-limiting embodiments, the step 824 may include determining whether there is a large discrepancy between the reference measurement RM3 and one or more of the sensor measurements SM1 and SM2. In non-limiting some embodiments, the transceiver 101 may determine whether the difference between the reference measurement RM3 and the sensor measurement SM1 is within a threshold amount and whether the difference between the reference measurement RM3 and the sensor measurement SM2 is within the threshold amount. In some non-limiting embodiments, the threshold amount may be a percentage of or deviation from sensor measurement SM1. In some non-limiting embodiments, the threshold amount may be a fixed, or the threshold amount may vary (e.g., based on the reference measurement RM3, sensor measurement SM1, or sensor measurement SM2). In some non-limiting embodiments, the step 824 may include determining whether the reference measurement RM3 is closer to the sensor measurement SM1 or to the sensor measurement SM2.

In some embodiments, in step 824, the transceiver 101 may determine that reference measurement RM3 is acceptable if the transceiver 101 determines both that (i) the difference between the reference measurement RM3 and the sensor measurement SM1, which was calculated without taking the unexpected reference measurement RM2 into account, is within the threshold amount and (ii) the reference measurement RM3 is closer to the sensor measurement SM1 than the sensor measurement SM2, which was calculated taking the unexpected reference measurement RM2 into account. However, this is not required, and, in some alternative embodiments, the transceiver 101 may determine that the reference measurement RM3 is acceptable in a different way. For example and without limitation, in one alternative embodiment, the transceiver 101 may determine that the reference measurement RM3 is acceptable if only one of conditions (i) and (ii) is met.

In some embodiments, in step 824, the transceiver 101 may determine that both reference measurements RM2 and RM3 are acceptable if the transceiver 101 determines both that (i) the difference between the reference measurement RM3 and the sensor measurement SM2, which was calculated taking the unexpected reference measurement RM2 into account, is within the threshold amount and (ii) the reference measurement RM3 is closer to the sensor measurement SM2 than the sensor measurement SM1, which was calculated without taking the unexpected reference measurement RM2 into account. However, this is not required, and, in some alternative embodiments, the transceiver 101 may determine that both reference measurements RM2 and RM3 are acceptable in a different way. For example and without limitation, in one alternative embodiment, the transceiver 101 may determine that the reference measurements RM2 and RM3 are acceptable if only one of conditions (i) and (ii) is met.

In some embodiments, in step 824, the transceiver 101 may be unable to determine that at least one of reference measurements RM2 and RM3 is acceptable if the difference between the reference measurement RM3 and the sensor measurement SM1 is outside the threshold amount and the difference between the reference measurement RM3 and the sensor measurement SM2 is outside the threshold amount.

In some embodiments, if the transceiver 101 determines in step 824 that the reference measurement RM3 is acceptable and that the unexpected reference measurement RM2 is not acceptable, the unexpected calibration process 800 may proceed from step 824 to a step 826 in which the transceiver 101 may accept only the reference measurement RM3 (and not the reference measurement RM2) as a calibration point. In some non-limiting embodiments, accepting the reference measurement RM3 as a calibration point may include storing the reference measurement RM3 in the calibration point memory. In some embodiments, in step 826, the transceiver 101 may calibrate the conversion function used to calculate analyte measurements from sensor data. In some non-limiting embodiments, the transceiver 101 may calibrate the conversion function using one or more of the calibration points stored in the calibration point memory. In some embodiments, the one or more calibration points used to calibrate the conversion function may include the reference measurement RM3. In some embodiments, the unexpected calibration process 800 may proceed from step 826 to a step 830 in which the transceiver 101 leaves the unexpected calibration phase and enters a normal calibration phase (e.g., the normal calibration phase 606 of FIG. 6). In the normal calibration phase, the transceiver 101 may use the updated conversion function to calculate sensor measurements from subsequent sensor data.

In some embodiments, if the transceiver 101 determines in step 824 that both reference measurements RM2 and RM3 are acceptable, the unexpected calibration process 800 may proceed from step 824 to a step 828 in which the transceiver 101 may accept the reference measurements RM2 and RM3 as calibration points. In some non-limiting embodiments, accepting the reference measurements RM2 and RM3 as calibration points may include storing the reference measurements RM2 and RM3 in the calibration point memory. In some embodiments, in step 828, the transceiver 101 may calibrate the conversion function used to calculate analyte measurements from sensor data. In some non-limiting embodiments, the transceiver 101 may calibrate the conversion function using one or more of the calibration points stored in the calibration point memory. In some embodiments, the one or more calibration points used to calibrate the conversion function may include the reference measurements RM2 and RM3. In some embodiments, the unexpected calibration process 800 may proceed from step 828 to a step 830 in which the transceiver 101 leaves the unexpected calibration phase and enters a normal calibration phase (e.g., the normal calibration phase 606 of FIG. 6). In the normal calibration phase, the transceiver 101 may use the updated conversion function to calculate sensor measurements from subsequent sensor data.

In some embodiments, if the transceiver 101 is unable to determine in step 824 that at least one of the reference measurements RM2 and RM3 is acceptable, the transceiver 101 may reject the reference measurements RM2 and RM3, and the unexpected calibration process 800 may proceed from step 824 to a step 832 in which the transceiver 101 leaves the unexpected calibration phase and enters a drop out phase (e.g., the drop out phase 610 of FIG. 6). However, this is not required, and, in some alternative embodiments, in step 832, the transceiver 101 may enter an initialization phase (e.g., the initialization phase 604 of FIG. 6) instead of entering the drop out phase. In some other alternative embodiments, instead of rejecting both reference measurements RM2 and RM3 and entering a drop out or initialization phase, the transceiver 101 may reject the reference measurement RM2, treat the reference measurement RM3 as unexpected, stay in the unexpected calibration phase, and try again one or more times to find one or more acceptable reference measurements using one or more additionally received reference measurements (e.g., a reference measurement RM4).

FIG. 9 is a flow chart illustrating an alternative unexpected calibration process 900, which may be performed during the unexpected calibration phase 608 of the control process 600 illustrated in FIG. 6. In some embodiments, the transceiver 101 may perform one or more steps of the alternative unexpected calibration process 900. In some non-limiting embodiments, the PIC microcontroller 920 of the transceiver 101 may perform one or more steps of the alternative unexpected calibration process 900.

In some embodiments, the alternative unexpected calibration process 900 may include a step 901 in which the transceiver 101 stores the unexpected reference measurement RM1 in a calibration point memory (e.g., a circular buffer). In some non-limiting embodiments, the alternative unexpected calibration process 900 may use the unexpected reference measurement RM1 as a calibration point in the calculation and display of subsequent sensor measurements (at least until a reference measurement RM2 is received). In some non-limiting embodiments, the alternative unexpected calibration process 900 may proceed from step 901 to a step 902.

In some embodiments, the alternative unexpected calibration process 900 may include a step 902 in which the transceiver 101 determines whether the transceiver 101 has received sensor data (e.g., light and/or temperature measurements) from the sensor 100. In some non-limiting embodiments, if the sensor has received sensor data, the alternative unexpected calibration process 900 may proceed from step 902 to a measurement calculation step 904. In some non-limiting embodiments, if the transceiver 101 has not received sensor data, the alternative unexpected calibration process 900 may proceed from step 902 to a step 906.

In some non-limiting embodiments, the alternative unexpected calibration process 900 may include the measurement calculation step 904. In some embodiments, the step 904 may include calculating a sensor measurement SM2 using the received sensor data and a conversion function that takes the unexpected reference measurement RM1 into account as a calibration point. In some embodiments, in step 904, the transceiver 101 may display the calculated sensor measurement SM2. In some non-limiting embodiments, the transceiver 101 may display the sensor measurement SM2 by transmitting it to the display device 105 for display.

In some embodiments, the alternative unexpected calibration process 900 may include a step 906 in which the transceiver 101 determines whether the transceiver 101 has received a reference measurement RM2. The reference measurement RM2 may be, for example and without limitation, an SMBG measurement obtained from, for example and without limitation, a finger-stick blood sample. In some non-limiting embodiments, the transceiver 101 may receive the reference measurement RM2 at least a period of time (e.g., 1 minute, 5 minutes, 10 minutes, 15 minutes, 30 minutes, 1 hour, etc.) after receiving the unexpected reference measurement RM1. In some embodiments, the transceiver 101 may receive the reference measurement RM2 from the display device 105. In some non-limiting embodiments, after the period of time has passed since the unexpected reference measurement RM1 was received, the transceiver 101 may cause the display device 105 to prompt a user for the reference measurement RM2, and, in response, the user may enter the reference measurement RM2 into the display device 105. If the transceiver 101 has not received a reference measurement RM2, the alternative unexpected calibration process 900 may proceed back to step 902 and continue using the calibration function that takes the reference measurement RM1 into account to calculate sensor measurements from sensor data until a reference measurement RM2 is received. If the transceiver 101 has received a reference measurement RM2, the alternative unexpected calibration process 900 may proceed to a step 908.

In some embodiments, the alternative unexpected calibration process 900 may include a step 908 in which the transceiver 101 calculates a sensor measurement SM1 using a conversion function that does not take the unexpected reference measurement RM1 into account as a calibration point. In some non-limiting embodiments, in step 908, the transceiver 101 may additionally calculate a sensor measurement SM2 using the conversion function that takes the unexpected reference measurement RM1 into account as a calibration point.

In some embodiments, the alternative unexpected calibration process 900 may include a step 910 in which the transceiver 101 determines whether one or more of the reference measurements RM1 and RM2 are acceptable. In some non-limiting embodiments, the step 910 may include comparing the reference measurement RM2 with the most-recent sensor measurement SM2, which was calculated by a conversion function that did take the unexpected reference measurement RM1 into account, and with the sensor measurement SM1, which was calculated by a conversion function that did not take the unexpected reference measurement RM1 into account.

In some non-limiting embodiments, the step 910 may include determining whether there is a large discrepancy between the reference measurement RM2 and one or more of the sensor measurements SM1 and SM2. In non-limiting some embodiments, the transceiver 101 may determine whether the difference between the reference measurement RM2 and the sensor measurement SM1 is within a threshold amount and whether the difference between the reference measurement RM2 and the sensor measurement SM2 is within the threshold amount. In some non-limiting embodiments, the threshold amount may be a percentage of or deviation from sensor measurement SM1. In some non-limiting embodiments, the threshold amount may be a fixed, or the threshold amount may vary (e.g., based on the reference measurement RM2, sensor measurement SM1, or sensor measurement SM2). In some non-limiting embodiments, the step 910 may include determining whether the reference measurement RM2 is closer to the sensor measurement SM1 or sensor measurement SM2.

In some embodiments, in step 910, the transceiver 101 may determine that reference measurement RM2 is acceptable if the transceiver 101 determines both that (i) the difference between the reference measurement RM2 and the sensor measurement SM1, which was calculated without taking the unexpected reference measurement RM1 into account, is within the threshold amount and (ii) the reference measurement RM2 is closer to the sensor measurement SM1 than the sensor measurement SM2, which was calculated taking the unexpected reference measurement RM1 into account. However, this is not required, and, in some alternative embodiments, the transceiver 101 may determine that the reference measurement RM2 is acceptable in a different way. For example and without limitation, in one alternative embodiment, the transceiver 101 may determine that the reference measurement RM2 is acceptable if only one of conditions (i) and (ii) is met.

In some embodiments, in step 910, the transceiver 101 may determine that both reference measurements RM1 and RM2 are acceptable if the transceiver 101 determines both that (i) the difference between the reference measurement RM2 and the sensor measurement SM2, which was calculated taking the unexpected reference measurement RM1 into account, is within the threshold amount and (ii) the reference measurement RM2 is closer to the sensor measurement SM2 than the sensor measurement SM1, which was calculated without taking the unexpected reference measurement RM1 into account. However, this is not required, and, in some alternative embodiments, the transceiver 101 may determine that both reference measurements RM1 and RM2 are acceptable in a different way. For example and without limitation, in one alternative embodiment, the transceiver 101 may determine that the reference measurements RM1 and RM2 are acceptable if only one of conditions (i) and (ii) is met.

In some embodiments, in step 910, the transceiver 101 may be unable to determine that at least one of reference measurements RM1 and RM2 is acceptable if the difference between the reference measurement RM2 and the sensor measurement SM1 is outside the threshold amount and the difference between the reference measurement RM2 and the sensor measurement SM2 is outside the threshold amount.

In some embodiments, if the transceiver 101 determines in step 910 that the reference measurement RM2 is acceptable and that the reference measurement RM1 is not acceptable, the alternative unexpected calibration process 900 may proceed from step 910 to a step 912 in which the transceiver 101 may accept only the reference measurement RM2 (and not the reference measurement RM1) as a calibration point. In some non-limiting embodiments, accepting only the reference measurement RM2 as a calibration point may include storing the reference measurement RM2 in the calibration point memory. In some non-limiting embodiments, accepting only the reference measurement RM2 as a calibration point may include removing or deleting the reference measurement RM1 from the calibration point memory.

In some embodiments, in step 912, the transceiver 101 may calibrate the conversion function used to calculate analyte measurements from sensor data. In some non-limiting embodiments, the transceiver 101 may calibrate the conversion function using one or more of the calibration points stored in the calibration point memory. In some embodiments, the one or more calibration points used to calibrate the conversion function may include the reference measurement RM2. In some embodiments, the alternative unexpected calibration process 900 may proceed from step 912 to a step 930 in which the transceiver 101 leaves the unexpected calibration phase and enters a normal calibration phase (e.g., the normal calibration phase 606 of FIG. 6). In the normal calibration phase, the transceiver 101 may use the updated conversion function to calculate sensor measurements from subsequent sensor data.

In some embodiments, if the transceiver 101 determines in step 910 that both reference measurements RM1 and RM2 are acceptable, the alternative unexpected calibration process 900 may proceed from step 910 to a step 914 in which the transceiver 101 may accept the reference measurements RM1 and RM2 as calibration points. In some non-limiting embodiments, accepting the reference measurements RM1 and RM2 as calibration points may include storing the reference measurement RM2 in the calibration point memory along with the reference measurement RM1, which was stored in the calibration point memory in step 902. In some embodiments, in step 914, the transceiver 101 may calibrate the conversion function used to calculate analyte measurements from sensor data. In some non-limiting embodiments, the transceiver 101 may calibrate the conversion function using one or more of the calibration points stored in the calibration point memory. In some embodiments, the one or more calibration points used to calibrate the conversion function may include the reference measurements RM1 and RM2. In some embodiments, the alternative unexpected calibration process 900 may proceed from step 914 to a step 930 in which the transceiver 101 leaves the unexpected calibration phase and enters a normal calibration phase (e.g., the normal calibration phase 606 of FIG. 6). In the normal calibration phase, the transceiver 101 may use the updated conversion function to calculate sensor measurements from subsequent sensor data.

In some embodiments, if the transceiver 101 is unable to determine in step 910 that at least one of the reference measurements RM1 and RM2 is acceptable, the alternative unexpected calibration process 900 may proceed to a step 915 in which the transceiver 101 may reject the reference measurement RM1, remove/delete the reference measurement RM1 from the calibration point memory, store the reference measurement RM2 in the calibration point memory, and treat the reference measurement RM2 as unexpected. In some embodiments, the alternative unexpected calibration process 900 may try again one or more times to find one or more acceptable reference measurements using one or more additionally received reference measurements. For example, in some non-limiting embodiments, the alternative unexpected calibration process 900 may proceed from step 915 to a step 916 in which the transceiver 101 determines whether the transceiver 101 has received sensor data (e.g., light and/or temperature measurements) from the sensor 100. In some non-limiting embodiments, if the sensor has received sensor data, the alternative unexpected calibration process 900 may proceed from step

916 to a measurement calculation step 918. In some non-limiting embodiments, if the transceiver 101 has not received sensor data, the alternative unexpected calibration process 900 may proceed from step 916 to a step 920.

In some non-limiting embodiments, the alternative unexpected calibration process 900 may include the measurement calculation step 918. In some embodiments, the step 918 may include calculating a sensor measurement SM2 using the received data and a calibration function that takes the unexpected reference measurement RM2 into account (but does not take the rejected reference measurement RM1 into account). In some embodiments, in step 918, the transceiver 101 may display the calculated sensor measurement SM2. In some non-limiting embodiments, the transceiver 101 may display the sensor measurement SM2 by transmitting it to the display device 105 for display.

In some embodiments, the alternative unexpected calibration process 900 may include a step 920 in which the transceiver 101 determines whether the transceiver 101 has received a reference measurement RM3. The reference measurement RM3 may be, for example and without limitation, an SMBG measurement obtained from, for example and without limitation, a finger-stick blood sample. In some non-limiting embodiments, the transceiver 101 may receive the reference measurement RM3 at least a period of time (e.g., 1 minute, 5 minutes, 10 minutes, 15 minutes, 30 minutes, 1 hour, etc.) after receiving the unexpected reference measurement RM2. In some embodiments, the transceiver 101 may receive the reference measurement RM3 from the display device 105. In some non-limiting embodiments, after the period of time has passed since the unexpected reference measurement RM2 was received, the transceiver 101 may cause the display device 105 to prompt a user for the reference measurement RM3, and, in response, the user may enter the reference measurement RM3 into the display device 105. If the transceiver 101 has not received a reference measurement RM3, the alternative unexpected calibration process 900 may proceed back to step 916 and continue using the calibration function that takes the reference measurement RM2 into account to calculate sensor measurements from sensor data until a reference measurement RM3 is received. If the transceiver 101 has received a reference measurement RM3, the alternative unexpected calibration process 900 may proceed from step 920 to a step 922.

In some embodiments, the alternative unexpected calibration process 900 may include a step 922 in which the transceiver 101 calculates a sensor measurement SM1 using a conversion function that takes the neither the unexpected reference measurement RM2 nor the rejected reference measurement RM1 into account as a calibration point. In some non-limiting embodiments, in step 922, the transceiver 101 may additionally calculate a sensor measurement SM2 using a conversion function that takes the unexpected reference measurement RM2 (but not the rejected reference measurement RM1) into account.

In some embodiments, the alternative unexpected calibration process 900 may include a step 924 in which the transceiver 101 determines whether one or more of the reference measurements RM2 and RM3 are acceptable. In some non-limiting embodiments, the step 924 may include comparing the reference measurement RM3 with the most-recent sensor measurement SM2, which was calculated by a conversion function that took the unexpected reference measurement RM2 into account, and with the sensor measurement SM1, which was calculated by a conversion function that did not take the unexpected reference measurement RM2 into account.

In some non-limiting embodiments, the step 924 may include determining whether there is a large discrepancy between the reference measurement RM3 and one or more of the sensor measurements SM1 and SM2. In non-limiting some embodiments, the transceiver 101 may determine whether the difference between the reference measurement RM3 and the sensor measurement SM1 is within a threshold amount and whether the difference between the reference measurement RM3 and the sensor measurement SM2 is within the threshold amount. In some non-limiting embodiments, the threshold amount may be a percentage of or deviation from sensor measurement SM1. In some non-limiting embodiments, the threshold amount may be a fixed, or the threshold amount may vary (e.g., based on the reference measurement RM3, sensor measurement SM1, or sensor measurement SM2). In some non-limiting embodiments, the step 924 may include determining whether the reference measurement RM3 is closer to the sensor measurement SM1 or to the sensor measurement SM2.

In some embodiments, in step 924, the transceiver 101 may determine that reference measurement RM3 is acceptable if the transceiver 101 determines both that (i) the difference between the reference measurement RM3 and the sensor measurement SM1, which was calculated without taking the unexpected reference measurement RM2 into account, is within the threshold amount and (ii) the reference measurement RM3 is closer to the sensor measurement SM1 than the sensor measurement SM2, which was calculated taking the unexpected reference measurement RM2 into account. However, this is not required, and, in some alternative embodiments, the transceiver 101 may determine that the reference measurement RM3 is acceptable in a different way. For example and without limitation, in one alternative embodiment, the transceiver 101 may determine that the reference measurement RM3 is acceptable if only one of conditions (i) and (ii) is met.

In some embodiments, in step 924, the transceiver 101 may determine that both reference measurements RM2 and RM3 are acceptable if the transceiver 101 determines both that (i) the difference between the reference measurement RM3 and the sensor measurement SM2, which was calculated taking the unexpected reference measurement RM2 into account, is within the threshold amount and (ii) the reference measurement RM3 is closer to the sensor measurement SM2 than the sensor measurement SM1, which was calculated without taking the unexpected reference measurement RM2 into account. However, this is not required, and, in some alternative embodiments, the transceiver 101 may determine that both reference measurements RM2 and RM3 are acceptable in a different way. For example and without limitation, in one alternative embodiment, the transceiver 101 may determine that the reference measurements RM2 and RM3 are acceptable if only one of conditions (i) and (ii) is met.

In some embodiments, in step 924, the transceiver 101 may be unable to determine that at least one of reference measurements RM2 and RM3 is acceptable if the difference between the reference measurement RM3 and the sensor measurement SM1 is outside the threshold amount and the difference between the reference measurement RM3 and the sensor measurement SM2 is outside the threshold amount.

In some embodiments, if the transceiver 101 determines in step 924 that the reference measurement RM3 is acceptable and that the unexpected reference measurement RM2 is not acceptable, the alternative unexpected calibration process 900 may proceed from step 924 to a step 926 in which the transceiver 101 may accept only the reference measurement RM3 (and not the reference measurement RM2) as a calibration point. In some non-limiting embodiments, accepting only the reference measurement RM3 as a calibration point may include storing the reference measurement RM3 in the calibration point memory. In some non-limiting embodiments, accepting only the reference measurement RM3 as a calibration point may include removing or deleting the reference measurement RM2 in the calibration point memory. In some embodiments, in step 926, the transceiver 101 may calibrate the conversion function used to calculate analyte measurements from sensor data. In some non-limiting embodiments, the transceiver 101 may calibrate the conversion function using one or more of the calibration points stored in the calibration point memory. In some embodiments, the one or more calibration points used to calibrate the conversion function may include the reference measurement RM3. In some embodiments, the alternative unexpected calibration process 900 may proceed from step 926 to a step 930 in which the transceiver 101 leaves the unexpected calibration phase and enters a normal calibration phase (e.g., the normal calibration phase 606 of FIG. 6). In the normal calibration phase, the transceiver 101 may use the updated conversion function to calculate sensor measurements from subsequent sensor data.

In some embodiments, if the transceiver 101 determines in step 924 that both reference measurements RM2 and RM3 are acceptable, the alternative unexpected calibration process 900 may proceed from step 924 to a step 928 in which the transceiver 101 may accept the reference measurements RM2 and RM3 as calibration points. In some non-limiting embodiments, accepting the reference measurements RM2 and RM3 as calibration points may include storing the reference measurement RM3 in the calibration point memory along with the reference measurement RM2, which was stored in the calibration point memory in step 915. In some embodiments, in step 928, the transceiver 101 may calibrate the conversion function used to calculate analyte measurements from sensor data. In some non-limiting embodiments, the transceiver 101 may calibrate the conversion function using one or more of the calibration points stored in the calibration point memory. In some embodiments, the one or more calibration points used to calibrate the conversion function may include the reference measurements RM2 and RM3. In some embodiments, the alternative unexpected calibration process 900 may proceed from step 928 to a step 930 in which the transceiver 101 leaves the unexpected calibration phase and enters a normal calibration phase (e.g., the normal calibration phase 606 of FIG. 6). In the normal calibration phase, the transceiver 101 may use the updated conversion function to calculate sensor measurements from subsequent sensor data.

In some embodiments, if the transceiver 101 is unable to determine in step 924 that at least one of the reference measurements RM2 and RM3 is acceptable, the transceiver 101 may reject the reference measurements RM2 and RM3 and remove/delete the reference measurement RM2 from the calibration point memory, and the alternative unexpected calibration process 900 may proceed from step 924 to a step 932 in which the transceiver 101 leaves the unexpected calibration phase and enters a drop out phase (e.g., the drop out phase 610 of FIG. 6). However, this is not required, and, in some alternative embodiments, in step 932, the transceiver 101 may enter an initialization phase (e.g., the initialization phase 604 of FIG. 6) instead of entering the drop out phase. In some other alternative embodiments, instead of rejecting both reference measurements RM2 and RM3 and entering a drop out or initialization phase, the transceiver 101 may reject the reference measurement RM2, remove or delete the reference measurement RM2 from the calibration point memory, store the reference measurement RM3 in the calibration point memory, treat the reference measurement RM3 as unexpected, stay in the unexpected calibration phase, and try again one or more times to find one or more acceptable reference measurements using one or more additionally received reference measurements (e.g., a reference measurement RM4).

FIG. 10 is a flow chart illustrating another alternative unexpected calibration process 1000, which may be performed during the unexpected calibration phase 608 of the control process 600 illustrated in FIG. 6. In some embodiments, the transceiver 101 may perform one or more steps of the other alternative unexpected calibration process 1000. In some non-limiting embodiments, the PIC microcontroller 920 of the transceiver 101 may perform one or more steps of the other alternative unexpected calibration process 1000.

In some embodiments, the other alternative unexpected calibration process 1000 may include one or more steps that are the same as or similar to steps included in the unexpected calibration process 800. For example, as shown in FIG. 10, the other alternative unexpected calibration process 1000 may include one or more of steps 802, 804, 806, 808, 812, 814, 816, 820, 826, 828, and 830, which are described above with reference to FIG. 8.

In some embodiments, the other alternative unexpected calibration process 1000 may include a step 1010, which may be the same as step 810 of the unexpected calibration process 800 except for one or more of the following differences. In step 1010, if the transceiver 101 is unable to determine that at least one of the reference measurements RM1 and RM2 is acceptable (e.g., because the transceiver 101 determines that (i) the difference between the reference measurement RM2 and the sensor measurement SM1 is outside the threshold amount and (ii) the difference between the reference measurement RM2 and the sensor measurement SM2 is outside the threshold amount), the transceiver 101 may treat the reference measurement RM2 as unexpected and proceed to a step 1015 in which the reference measurement RM1 is accepted (instead of rejecting the reference measurement as in step 808 of the unexpected calibration process 800).

In some embodiments, in step 1015, the transceiver 101 may accept the reference measurement RM1 as a calibration point. In some non-limiting embodiments, accepting the reference measurement RM1 as a calibration point may include storing the reference measurement RM1 in a calibration point memory (e.g., a circular buffer). In some embodiments, in step 1015, the transceiver 101 may calibrate the conversion function used to calculate analyte measurements from sensor data. In some non-limiting embodiments, the transceiver 101 may calibrate the conversion function using one or more of the calibration points stored in the calibration point memory. In some embodiments, the one or more calibration points used to calibrate the conversion function may include the reference measurement RM1. In some embodiments, the other alternative unexpected calibration process 1000 may proceed from step 1015 and try again one or more times to find one or more acceptable reference measurements using one or more additionally received reference measurements.

In some embodiments, the other alternative unexpected calibration process 1000 may include a measurement calculation step 1018, which may be performed if the transceiver 101 determines that it has received sensor data (e.g., light and/or temperature measurements) from the sensor 100 in step 816. In some embodiments, step 1018 may be the same as step 818 of the unexpected calibration process 800 except for one or more of the following differences. In some embodiments, the step 1018 may include calculating a sensor measurement SM1 using the current calibration function, which takes the reference measurement RM1 into account but does not take the unexpected reference measurement RM2 into account, and the received sensor data. In some embodiments, in step 1018, the transceiver 101 may display the calculated sensor measurement SM1. In some non-limiting embodiments, the transceiver 101 may display the sensor measurement SM1 by transmitting it to the display device 105 for display.

In some embodiments, the other alternative unexpected calibration process 1000 may include a measurement calculation step 1022, which may be performed if the transceiver 101 determines that the transceiver 101 has received a reference measurement RM3 in step 820. In some embodiments, step 1022 may be the same as step 822 of the unexpected calibration process 800 except for one or more of the following differences. In some embodiments, in step 1022, the transceiver 101 may calculate a sensor measurement SM2 using a conversion function that takes the unexpected reference measurement RM2 (and the reference measurement RM1) into account as a calibration point. In some non-limiting embodiments, in step 1022, the transceiver 101 may additionally calculate a sensor measurement SM1 using a conversion function that takes into account the reference measurement RM1 (but not the reference measurement RM2) as a calibration point.

In some embodiments, the other alternative unexpected calibration process 1000 may include a step 1024, which may be the same as step 824 of the unexpected calibration process 800 except for one or more of the following differences. In step 1024, if the transceiver 101 is unable to determine that at least one of the reference measurements RM2 and RM3 is acceptable, the transceiver 101 may reject the reference measurements RM2 and RM3, and the other alternative unexpected calibration process 1000 may proceed from step 1024 to a step 1032 in which the transceiver 101 leaves the unexpected calibration phase and enters a drop out phase (e.g., the drop out phase 610 of FIG. 6). However, this is not required, and, in some alternative embodiments, in step 1032, the transceiver 101 may enter an initialization phase (e.g., the initialization phase 604 of FIG. 6) instead of entering the drop out phase. In some other alternative embodiments, instead of rejecting both reference measurements RM2 and RM3 and entering a drop out or initialization phase, the transceiver 101 may accept the reference measurement RM2, treat the reference measurement RM3 as unexpected, stay in the unexpected calibration phase, and try again one or more times to find one or more acceptable reference measurements using one or more additionally received reference measurements (e.g., a reference measurement RM4).

FIG. 11 is a flow chart illustrating an additional alternative unexpected calibration process 1100, which may be performed during the unexpected calibration phase 608 of the control process 600 illustrated in FIG. 6. In some embodiments, the transceiver 101 may perform one or more steps of the additional alternative unexpected calibration process 1100. In some non-limiting embodiments, the PIC micro-controller 920 of the transceiver 101 may perform one or more steps of the additional alternative unexpected calibration process 1100.

In some embodiments, the additional alternative unexpected calibration process 1100 may include one or more steps that are the same as or similar to steps included in the alternative unexpected calibration process 900. For example, as shown in FIG. 11, the additional alternative unexpected calibration process 1100 may include one or more of steps 901, 902, 904, 906, 908, 912, 914, 916, 920, 926, 928, and 930, which are described above with reference to FIG. 9.

In some embodiments, the additional alternative unexpected calibration process 1100 may include a step 1110, which may be the same as step 910 of the alternative unexpected calibration process 900 except for one or more of the following differences. In step 1110, if the transceiver 101 is unable to determine that at least one of the reference measurements RM1 and RM2 is acceptable (e.g., because the transceiver 101 determines that (i) the difference between the reference measurement RM2 and the sensor measurement SM1 is outside the threshold amount and (ii) the difference between the reference measurement RM2 and the sensor measurement SM2 is outside the threshold amount), the transceiver 101 may proceed to a step 1115 in which the reference measurement RM1 is accepted (instead of being rejected and removed/deleted from the calibration point memory as in step 915 of the alternative unexpected calibration process 900).

In some embodiments, in step 1115, the transceiver 101 may accept the reference measurement RM1, store the reference measurement RM2 in the calibration point memory (e.g., a circular buffer), and treat the reference measurement RM2 as unexpected. In some embodiments, the additional alternative unexpected calibration process 1100 may try again one or more times to find one or more acceptable reference measurements using one or more additionally received reference measurements.

In some non-limiting embodiments, the additional alternative unexpected calibration process 1100 may include the measurement calculation step 1118. In some embodiments, the step 1118 may include calculating a sensor measurement SM2 using the received data and a calibration function that takes the unexpected reference measurement RM2 (and the accepted reference measurement RM1) into account. In some embodiments, in step 1118, the transceiver 101 may display the calculated sensor measurement SM2. In some non-limiting embodiments, the transceiver 101 may display the sensor measurement SM2 by transmitting it to the display device 105 for display.

In some embodiments, the additional alternative unexpected calibration process 1100 may include a step 1122 in which the transceiver 101 calculates a sensor measurement SM1 using a conversion function that does not take the unexpected reference measurement RM2 into account (but does take the accepted reference measurement RM1 into account) as a calibration point. In some non-limiting embodiments, in step 1122, the transceiver 101 may additionally calculate a sensor measurement SM2 using a conversion function that takes the unexpected reference measurement RM2 (and the rejected reference measurement RM1) into account.

In some embodiments, the additional alternative unexpected calibration process 1100 may include a step 1124, which may be the same as step 924 of the alternative unexpected calibration process 900 except for one or more of the following differences. In step 1124, if the transceiver

101 is unable to determine that at least one of the reference measurements RM2 and RM3 is acceptable, the transceiver 101 may reject the reference measurements RM2 and RM3 and remove/delete the reference measurement RM2 from the calibration point memory, and the additional alternative unexpected calibration process 1100 may proceed from step 1124 to a step 1132 in which the transceiver 101 leaves the unexpected calibration phase and enters a drop out phase (e.g., the drop out phase 610 of FIG. 6). However, this is not required, and, in some alternative embodiments, in step 1132, the transceiver 101 may enter an initialization phase (e.g., the initialization phase 604 of FIG. 6) instead of entering the drop out phase. In some other alternative embodiments, instead of rejecting both reference measurements RM2 and RM3 and entering a drop out or initialization phase, the transceiver 101 may accept the reference measurement RM2, store the reference measurement RM3 in the calibration point memory, treat the reference measurement RM3 as unexpected, stay in the unexpected calibration phase, and try again one or more times to find one or more acceptable reference measurements using one or more additionally received reference measurements (e.g., a reference measurement RM4).

FIG. 12 is a flow chart illustrating an alternative process 1200 for controlling initialization and calibration of an analyte monitoring system 50. In some embodiments, the transceiver 101 may perform one or more steps of the alternative control process 1200. In some non-limiting embodiments, the PIC microcontroller 920 of the transceiver 101 may perform one or more steps of the alternative control process 1200. In some embodiments, the alternative process 1200 may begin after insertion or implantation of the analyte sensor 100.

In some embodiments, the alternative control process 1200 may include one or more phases that are the same as or similar to phases included in the control process 600 described above with reference to FIG. 6. For example, as shown in FIG. 12, the alternative control process 1200 may include one or more of phases 602, 604, 608, and 610, which are described above with reference to FIG. 6.

In some embodiments, the alternative control process 1200 may include one or more of a warm up phase 602, an initialization phase 604, a normal calibration phase 1206, an unexpected calibration phase 608, a drop out phase 610, and an expected calibration phase 1212. In some non-limiting embodiments, after sensor insertion or implantation, the alternative control process 1200 may proceed from the warm up phase 602 to the initialization phase 604 and then to the normal calibration phase 1206. In some embodiments, the normal calibration phase 1206 of the alternative control process 1200 may be the same as the normal calibration phase 606 of the control process 600 except that the normal calibration phase 1206 may additionally determine whether an accepted reference measurement is an expected reference measurement.

In some embodiments, in the normal calibration phase 1206, the transceiver 101 may determine whether an accepted reference measurement is an expected reference measurement based on a comparison of the accepted reference measurement to the most-recent sensor measurement (i.e., the most-recent analyte measurement calculated by the conversion function using received sensor data). In some embodiments, if there is no more than a small discrepancy between the accepted reference measurement and the most-recent sensor measurement, the transceiver 101 may determine that the accepted reference measurement is an expected reference measurement and proceed to an expected calibration phase 1212.

In some embodiments, during the expected calibration phase 1212, the transceiver 101 may lower the frequency at which reference measurements are received (relative to the frequency at which reference measurements are received in the normal calibration phase 1206). For example, in some non-limiting embodiments, in the expected calibration phase 1212, the transceiver 101 may cause the display device 105 to prompt a user for reference measurements less frequently than a rate at which the display device 105 prompts a user for reference measurements in the normal calibration phase 1206. In some non-limiting embodiments, the user may enter one or more reference measurements into the display device 105 in response to the prompts, and the display device 105 may convey the one or more reference measurements to the transceiver 101.

In some embodiments, in the expected calibration phase 1212, the transceiver 101 may determine whether to accept a received reference measurement or to treat the reference measurement as unexpected. In some non-limiting embodiments, the transceiver 101 may determine whether to accept a received reference measurement by comparing the reference measurement to the most-recent sensor measurement (i.e., the most-recent analyte measurement calculated by the conversion function using received sensor data). In some embodiments, if the transceiver 101 determines that a reference measurement is unexpected, the alternative control process 1200 may proceed from the expected calibration phase 1212 to an unexpected calibration phase 608. In some embodiments, if the transceiver 101 determines that the reference measurement is acceptable, the transceiver 101 may calibrate (or re-calibrate or update) the conversion function using the reference point as a calibration point. In some embodiments, the transceiver 101 may determine whether an accepted reference measurement is an expected reference measurement. In some embodiments, if the transceiver 101 determines that the reference measurement is expected, the alternative control process 1200 may stay in the expected calibration phase 1212. In some embodiments, if the transceiver 101 does not determine that the reference measurement is expected, the alternative control process 1200 may proceed from the expected calibration phase 1212 to a normal calibration phase 1206.

FIG. 13 is a flow chart illustrating an alternative normal calibration process 1300, which may be performed during the normal calibration phase 1206 of the alternative control process 1200 illustrated in FIG. 12. In some embodiments, the transceiver 101 may perform one or more steps of the alternative normal calibration process 1300. In some non-limiting embodiments, the PIC microcontroller 920 of the transceiver 101 may perform one or more steps of the alternative normal calibration process 1300.

In some embodiments, the alternative normal calibration process 1300 may include one or more steps that are the same as or similar to steps included in the normal calibration process 700 described above with reference to FIG. 7. For example, as shown in FIG. 13, the alternative normal calibration process 1300 may include one or more of steps 702, 704, 706, 708, 710, and 712, which are described above with reference to FIG. 7. In some embodiments, the alternative normal calibration process 1300 may additionally include steps 1314 and 1316.

In some non-limiting embodiments, in step 1314, the transceiver 101 may determine whether an accepted reference measurement RM1 is expected. In some non-limiting embodiments, the step 1314 may reuse the results of the comparison of the reference measurement RM1 and the most-recent sensor measurement SM1 (i.e., the most-recent analyte measurement calculated by the conversion function using received sensor data) that was performed in step 708. However, this is not required, and, in some alternative embodiments, step 1314 may include performing its own comparison. In some non-limiting embodiments, the step 1314 may include determining whether there is no more than a small discrepancy between the reference measurement RM1 and the most-recent sensor measurement SM1. In some non-limiting embodiments, the transceiver 101 may determine that a reference measurement RM1 is expected if there is no more than a small discrepancy between the reference measurement RM1 and the most-recent sensor measurement SM1. In non-limiting some embodiments, the transceiver 101 may determine that the reference measurement is expected if the difference between the reference measurement RM1 and the sensor measurement SM1 is within a threshold amount. In some non-limiting embodiments, the threshold amount may be a percentage of the sensor measurement SM1 (e.g., ±5% of SM1) or a deviation of the sensor measurement SM1 (e.g., ±3 mg/dL of SM1).

In some non-limiting embodiments, the threshold amount may be a fixed threshold. However, this is not required, and, in some alternative embodiments, the threshold amount may vary. In some non-limiting alternative embodiments, the threshold amount may vary based on one or more of the sensor measurement SM1 and the reference measurement RM1. In some non-limiting embodiments where the threshold amount varies based on reference amount RM1, the reference measurement range may be divided into two or more sub-ranges, and the transceiver 101 may use a different threshold for each of the sub-ranges. That is, in some non-limiting embodiments, if the reference measurement RM1 falls into a second reference measurement sub-range, the transceiver 101 may use a second threshold when determining whether the reference measurement RM1 is acceptable. For example and without limitation, in one non-limiting alternative embodiment where the threshold amount varies based on reference measurement sub-ranges, the reference measurement range may be divided into the following five sub-ranges: (i) less than 70 mg/dL, (ii) greater than or equal to 70 mg/dL and less than 140 mg/dL, (iii) greater than or equal to 140 mg/dL and less than 180 mg/dL, (iv) greater than or equal to 180 mg/dL and less than 240 mg/dL, and (v) greater than or equal to 240 mg/dL, and the transceiver 101 may use a different threshold amount for each of the five sub-ranges. However, this is not required, and some alternative embodiments may use different sub-ranges and/or a different number of sub-ranges. In some other alternative embodiments having a varying threshold amount, the transceiver 101 may use a linear or non-linear formula to calculate the threshold amount that should be used for a particular reference measurement RM1 or sensor measurement SM1.

In some embodiments, if the transceiver 101 determines that the reference measurement RM1 is expected, the alternative normal calibration process 1300 may proceed from step 1314 to step 1316 in which the transceiver 101 leaves the normal calibration phase and enters an expected calibration phase (e.g., the expected calibration phase 1212 of FIG. 12). In some embodiments, if the transceiver 101 does not determine that the reference measurement RM1 is expected, the alternative normal calibration process 1300 may proceed from step 1314 to step 702.

FIG. 14 is a flow chart illustrating an expected calibration process 1400, which may be performed during the expected calibration phase 1212 of the alternative control process 1200 illustrated in FIG. 12. In some embodiments, the transceiver 101 may perform one or more steps of the expected calibration process 1400. In some non-limiting embodiments, the PIC microcontroller 920 of the transceiver 101 may perform one or more steps of the expected calibration process 1400.

In some embodiments, the expected calibration process 1400 may include one or more steps that are the same as or similar to steps included in the normal calibration process 700 described above with reference to FIG. 7. For example, as shown in FIG. 14, the expected calibration process 1400 may include one or more of steps 702, 704, 706, 708, 710, and 712, which are described above with reference to FIG. 7. In some embodiments, the expected calibration process 1400 may additionally include steps 1401, 1414, 1416, and 1418.

In some non-limiting embodiments, in step 1401, the transceiver 101 may lower the frequency at which reference measurements are received (relative to the frequency at which reference measurements are received in the normal calibration phase 1206). For example, in some non-limiting embodiments, in the expected calibration phase 1212, the transceiver 101 may cause the display device 105 to prompt a user for reference measurements less frequently than a rate at which the display device 105 prompts a user for reference measurements in the normal calibration phase 1206. For example and without limitation, in some non-limiting embodiments, the transceiver 101 may lower the frequency at which reference measurements are received to approximately every 18 hours or approximately every 24 hours (compared to, for example and without limitation, approximately every 12 hours in the normal calibration phase 1206). In some non-limiting embodiments, the user may enter one or more reference measurements into the display device 105 in response to the prompts, and the display device 105 may convey the one or more reference measurements to the transceiver 101.

In some non-limiting embodiments, in step 1414, the transceiver 101 may determine whether an accepted reference measurement RM1 is expected. In some non-limiting embodiments, step 1414 of the expected calibration process 1400 may be the same as step 1314 of the alternative normal calibration process 1300 except for the following differences. First, if the transceiver 101 determines that the reference measurement RM1 is expected in step 1414, the expected calibration process 1400 may proceed to step 702. Second, if the transceiver 101 does not determine that the reference measurement RM1 is expected in step 1414, the expected calibration process 1400 may proceed to a step 1416 in which the transceiver 101 increases the frequency at which reference measurements are received (e.g., by returning frequency to that used in the normal calibration phase 1206) before returning to the normal calibration phase 1206 in step 1418.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. An analyte monitoring method comprising:
   using a light source of an analyte sensor of an analyte monitoring system to emit excitation light that interacts with indicator molecules of an analyte indicator of the analyte sensor;
   using the indicator molecules of the analyte indicator with which the excitation light interacts to emit emission light;
   using the analyte sensor to generate sensor data indicative of an amount or concentration of an analyte in proximity to the analyte indicator, wherein using the analyte sensor to generate the sensor data comprises using a photodetector of the analyte sensor to generate a measurement indicative of a level of the emission light emitted by the indicator molecules;
   using a transceiver interface device of the analyte sensor to convey the sensor data;
   using a sensor interface device of a transceiver of the analyte monitoring system to receive the sensor data conveyed by the analyte sensor;
   using the transceiver to receive a first reference analyte measurement (RM1);
   using a processor of the transceiver to determine that the RM1 is unexpected;
   after determining that the RM1 is unexpected, using the transceiver to receive a second reference analyte measurement (RM2);
   using the processor of the transceiver to use the sensor data to calculate a first sensor analyte measurement (SM1) without the RM1 as a calibration point;
   using the processor of the transceiver to use the sensor data to calculate a second sensor analyte measurement (SM2) with the RM1 as a calibration point;
   using the processor of the transceiver to determine that the RM2 is unexpected, wherein determining that the RM2 is unexpected comprises comparing the RM2 with the SM1 and comparing the RM2 with the SM2;
   after determining that the RM2 is unexpected, using the transceiver to receive a third reference analyte measurement (RM3);
   using the processor of the transceiver to accept one or more of the RM2 and the RM3 as calibration points; and
   using the processor of the transceiver to calibrate the analyte sensor using at least one or more of the RM2 and the RM3 as calibration points.

2. The method of claim 1, further comprising, after determining that the RM2 is unexpected, accepting the RM1.

3. The method of claim 1, further comprising, after determining that the RM2 is unexpected, rejecting the RM1.

4. The method of claim 1, wherein accepting one or more of the RM2 and the RM3 as calibration points comprises accepting both the RM2 and the RM3 as calibration points.

5. The method of claim 4, wherein calibrating the analyte sensor uses at least the RM2 and the RM3 as calibration points.

6. The method of claim 1, wherein accepting one or more of the RM2 and the RM3 as calibration points comprises storing one or more of the RM2 and the RM3 in a calibration point memory.

7. The method of claim 1, wherein calibrating the analyte sensor comprises calibrating a conversion function used to convert sensor data received from the analyte sensor into a sensor analyte measurement.

8. The method of claim 1, wherein determining that the RM2 is unexpected comprises determining that a difference between the RM2 and the SM1 is not within a threshold amount and determining that a difference between the RM2 and the SM2 is not within a threshold amount.

9. The method of claim 1, further comprising:
   using the analyte sensor to generate and convey second sensor data indicative of a second amount or concentration of the analyte in proximity to the analyte indicator of the analyte sensor;
   using the transceiver to receive the second sensor data conveyed by the analyte sensor;
   using the transceiver to use the second sensor data to calculate a third sensor analyte measurement (SM3) without the RM2 as a calibration point; and
   using the transceiver to use the second sensor data to calculate a second fourth sensor analyte measurement (SM4) with the RM2 as a calibration point.

10. The method of claim 9, wherein accepting one or more of the RM2 and the RM3 as calibration points comprises:
    determining that the difference between the RM3 and the SM3 is within a threshold amount; and
    determining that the RM3 is closer to the SM3 than to the SM4.

11. The method of claim 10, wherein accepting one or more of the RM2 and the RM3 as calibration points comprises accepting the RM3 as a calibration point and not accepting the RM2 as a calibration point.

12. The method of claim 11, wherein calibrating the analyte sensor uses at least the RM3 as a calibration point and does not use the RM2 as a calibration point.

13. An analyte monitoring system comprising:
    an analyte sensor comprising:
       an analyte indicator comprising indicator molecules;
       a light source configured to emit excitation light that interacts with the indicator molecules;
       a photodetector; and
       a transceiver interface device, wherein the analyte sensor is configured to generate sensor data indicative of an amount or concentration of an analyte in proximity to the analyte indicator, generating the sensor data comprises using the photodetector to generate a measurement indicative of a level of emission light emitted by the indicator molecules, and the transceiver interface device is configured to convey the sensor data;
    a transceiver comprising:
       a sensor interface device configured to receive the sensor data conveyed by the analyte sensor; and
       a display interface device configured to convey information to a display device and to receive information from the display device; and
       a processor configured to:
          receive a first reference analyte measurement (RM1) from the display device via the display interface device;
          determine that the RM1 is unexpected;
          after determining that the RM1 is unexpected, receive a second reference analyte measurement (RM2) from the display device via the display interface device;
          use the sensor data to calculate a first sensor analyte measurement (SM1) without the RM1 as a calibration point;
          use the sensor data to calculate a second sensor analyte measurement (SM2) with the RM1 as a calibration point;

determine that the RM2 is unexpected, wherein determining that the RM2 is unexpected comprises comparing the RM2 with the SM1 and comparing the RM2 with the SM2;

after determining that the RM2 is unexpected, receive a third reference analyte measurement (RM3) from the display device via the display interface device;

accept one or more of the RM2 and the RM3 as calibration points; and calibrate the analyte sensor using at least one or more of the RM2 and the RM3 as calibration points.

14. The analyte monitoring system of claim 13, wherein the sensor interface device comprises an antenna configured to receive wirelessly the sensor data from the analyte sensor.

15. The analyte monitoring system of claim 13, wherein the analyte sensor is further configured to generate second sensor data indicative of a second amount or concentration of the analyte in proximity to the analyte indicator, and the processor is further configured to:

use the second sensor data to calculate a third sensor analyte measurement (SM3) without the RM2 as a calibration point; and use the second sensor data to calculate a fourth sensor analyte measurement (SM4) with the the RM2 as a calibration point.

16. The analyte monitoring system of claim 15, wherein accepting one or more of the RM2 and the RM3 as calibration points comprises:

determining that the difference between the RM3 and the SM3 is within a threshold amount; and determining that the RM3 is closer to the SM3 than to the SM4.

17. The analyte monitoring system of claim 16, wherein accepting one or more of the RM2 and the RM3 as calibration points comprises accepting the RM3 as a calibration point and not accepting the RM2 as a calibration point.

18. The analyte monitoring system of claim 17, wherein calibrating the analyte sensor uses at least the RM3 as a calibration point and does not use the RM2 as a calibration point.

19. The analyte monitoring system of claim 13, wherein the processor is further configured to, after determining that the RM2 is unexpected, accept the RM1.

20. The analyte monitoring system of claim 13, wherein the processor is further configured to, after determining that the RM2 is unexpected, reject the RM1.

21. The analyte monitoring system of claim 13, wherein the transceiver interface device comprises an inductor, and a sensor interface device comprises an inductor.

* * * * *